United States Patent [19]
van der Bruggen et al.

[11] Patent Number: 5,965,381
[45] Date of Patent: Oct. 12, 1999

[54] DELIVERY OF PROTEINS INTO EUKARYOTIC CELLS WITH RECOMBINANT YERSINIA

[75] Inventors: Pierre B. van der Bruggen, Corroy-Le-Grand; Guy R. Cornelis, Kraainem; Anne M. Boland; Thierry R. Boon-Falleur, both of Brussels, all of Belgium

[73] Assignees: Ludwig Institute for Cancer Research, New York, N.Y.; Universite Catholique de Louvain, Louvain-la-Neuve, Belgium

[21] Appl. No.: 09/036,582

[22] Filed: Mar. 6, 1998

[51] Int. Cl.$^6$ .............................. C12N 1/21; C12N 15/74; C12Q 1/02; C07K 14/24

[52] U.S. Cl. ........................... 435/29; 435/69.1; 435/69.3; 435/252.1; 435/252.3; 435/320.1; 435/373; 435/480; 424/93.2

[58] Field of Search .............................. 435/252.3, 320.1, 435/69.1, 480, 252.1, 69.3, 373, 29; 424/93.2

[56] References Cited

U.S. PATENT DOCUMENTS

| | | | |
|---|---|---|---|
| 5,342,774 | 8/1994 | Boon et al. | 435/371 |
| 5,405,940 | 4/1995 | Boon et al. | 530/328 |
| 5,530,096 | 6/1996 | Wolfel et al. | 530/328 |

OTHER PUBLICATIONS

Michiels et al., J. Bacteriology 173(16):4994–5009 (1991).

G.R. Cornelis and H. Wolf–Watz (1997) "The Yersinia Yop Virulon: A Bacterial System for Subverting Eukaryotic Cells" *Molecular Microbiology* 23 (5): 861–867.

V.L. Miller and S. Falkow (1988) "Evidence for Two Genetic Loci in *Yersinia Enterocolitica* That Can Promote Invasion of Epithelial Cells" *Infect. Immun.* 56 (5): 1242–1248.

R. Rosqvist et al. (1991) "Intracellular Targeting of the Yersinia YopE Cytotoxin in Mammalian Cells Induces Actin Microfilament Disruption" *Infect. Immun.* 59 (2): 4562–4569.

E.L. Hartland et al. (1994) "Essential Role of YopD in Inhibition of the Respiratory Burst of Macrophages by *Yersinia enterocolitica*" *Infect Immun.* 62 (10): 4445–4453.

R. Rosqvist et al. (1988) "Inhibition of Phagocytosis in Yersinia pseudotuberculosis: A Virulence Plasmid–encoded Ability Involving the Yop2b Protein" *Infect. Immun.* 56 (8): 2139–2143.

J. Bliska and D.S. Black (1995) "Inhibition of the Fc Receptor–mediated Oxidative Burst in Macrophages by the Yersinia pseudotuberculosis Tyrosine Phosphatase" *Infect. Immun.* 63 (2): 681–685.

S. Hakansson et al. (1996) "The Yersinia YpkA Ser/Thr Kinase is Translocated and Subsequently Targeted to the Inner Surface of the HeLa Cell Plasma Membrane" *Mol. Microbiol.* 20 (3): 593–603.

K.Y. Leung and S.C. Straley (1989) "The yopM Gene of *Yersinia pestis* Encodes a Released Protein Having Homology With the Human Platelet Surface Protein GPIb" *J. Bacterial.* 171 (9): 4623–4632.

S.D. Mills et al. (1997) "Yersinia enterocolitica Induces Apoptosis in Macrophages . . . " *Proc. Natl. Acad. Sci. USA* 94: 12638–12643.

M. Sory et al. (1995) "Identification of the YopE and YopH Domains Required for Secretion . . . " *Proc. Natl. Acad. Sci. USA* 92: 11998–12002.

A. Boland et al. (1996) "Status of YopM and YopN in the Yersinia Yop Virulon . . . " *The EMBO Journal* 15 (19): 5191–5201.

J.B. Van den Eynde and P. van der Bruggen (1997) "T cell Defined Tumor Antigens" *Current Opinion in Immunology* 9: 684–693.

U. Sahin et al. (1997) "Serological Identification of Human Tumor Antigens" *Current Opinion in Immunology* 9: 709–716.

D.L. Shawler et al. (1997) "Gene Therapy Approaches to Enhance Antimumor Immunity" *Advances in Pharmacology* 40: 309–337.

K. Kaniga et al. (1991) "A Wide–host–range Suicide Vector for Improving Reverse Genetics in Gram–nega Bacteria: Inactivation of the bla4 gene of *Yersinia enterocolitica*" *Gene* 109: 137–141.

M.R. Sarker and G.R. Cornelis (1997) "Direct Repeat Sequences in the cagA Gene of *Helicobacter pylori*: A Ghost of a Chance Encounter?" *Molecular Microbiology* 23 (2): 409–411.

M.P. Sory and G.R. Cornelis (1994) "Translocation of a Hybrid YopE–adenylate Cyclase From *Yersinia Enterocolitica* into HeLa Cells" *Molecular Microbiology* 14(3): 583–594.

S.A. Thompson et al. (1995) "Minimal Epitopes Expressed in a Recombinant Polyepitope Protein . . . " *Proc. Natl. Acad. Sci. USA* 92: 5845–5849.

S.C. Gilbert et al. (1997) "A Protein Particle Vaccine Containing Multiple Malaria Epitopes" *Nature Biotechnology* 15: 1280–1284.

O. Türeci et al. (1997) "Serological Analysis of Human Tumor Antigens: Molecular Definition and Implications" *Molecular Medicine Today* 3 (8): 342–349.

*Primary Examiner*—Johnny F. Railey, II
*Attorney, Agent, or Firm*—Scully, Scott, Murphy & Presser

[57] ABSTRACT

The present invention relates to recombinant Yersinia and the use thereof for delivery of proteins into eukaryotic cells, including related compositions and methods of treatment and related assays.

64 Claims, 8 Drawing Sheets

FIGURE 2(B)

```
1     aaaaatggcc aaaaactttc aatggtagaa gagctaaatt tggataagta acgcataaaa
61    attttcgacg aaaaactata tatatatata tatttaatat gtatggtttc atttgcaatg
121   aaaaaaccga taataaagat attttcagaa aggcattcaa tatgtttata aacccaagaa
181   atgtatctaa tacttttttg caagaaccat tacgtcattc ttctgattta actgagatgc
241   cagttgaggc agaaaatgtt aaatctaagg ctgaatatta taatgcatgg tcggaatggg
301   aacgaaatgc ccctccgggg aatggtgaac agaggggaat ggcggtttca aggttacgcg
361   attgcctgga ccgacaagcc catgagctag aactaaataa tctggggctg agttctttgc
421   cggaattacc tccgcattta gagagtttag tggcgtcatg taattctctt acagaattac
481   cggaattgcc gcagagcctg aaatcacttc aagttgataa taacaatctg aaggcattat
541   ccgatttacc tcctttactg gaatatttag gtgccgctaa taatcagctg gaagaattac
601   cagagttgca aaactcgtcc ttcttgacat ctattgatgt tgataacaat tcactgaaaa
661   cattacctga tttacctcct tcactggaat ttcttgctgc tggtaataat cagctggaag
721   aattgtcaga gttgcaaaac ttgcccttct tgactgcgat ttatgctgat aacaattcac
781   tgaaaacatt acccgattta cccccttccc tgaaaacact taatgtcaga gaaaattatt
841   taactgatct gccagaatta ccgcagagtt taaccttctt agatgtttct gataatattt
901   tttctggatt atcggaattg ccaccaaact tgtataatct caatgcatcc agcaatgaaa
961   taagatcttt atgcgattta cccccttcac tggtagaact tgatgtcaga gataatcagt
1021  tgatcgaact gccagcgtta cctccacgct tagaacgttt aatcgcttca tttaatcatc
1081  ttgctgaagt acctgaattg ccgcaaaacc tgaaactgct ccacgtagag tacaacgctc
1141  tgagagagtt tcccgatata cctgagtcag tggaagatct tcggatggac tctgaacgtg
1201  taattgatcc atatgaattt gctcatgaga ctatagacaa acttgaagat gatgtatttg
1261  agtagtgcgc aagagcgttc ataattctgc gtcacgttaa aatatcatta caacgtaatc
1321  actttatcga
```

FIGURE 3

```
1     gaattcccca actttgacac cgataaccgg ttcaatagta tctggaatag acagcgaaag
61    ttgttgaaat aattgagtga tagcttgttc aaatgaatac atttgatctc ctaatagtta
121   gataaaatat caacttaacc aaagcactct cggcagacca tcaattttag cctataattt
181   ttagttttta ttttgtctaa tataacaaca aaaacagcag cggtttttta tataaccacc
241   ggctattttc ccactaagat aaccttgttt taatagccaa gggaataaat agtcatgaaa
301   atatcatcat ttatttctac atcactgccc ctgccggcat cagtgtcagg atctagcagc
361   gtaggagaaa tgtctgggcg ctcagtctca cagcaaaaaa gtgatcaata tgcaaacaat
421   ctggccgggc gcactgaaag ccctcagggt tccagcttag ccagccgtat cattgagagg
481   ttatcatcaa tggcccactc tgtgattgga tttatccaac gcatgttctc ggaggggagc
541   cataaaccgg tggtgacacc agcactcacg cctgcacaaa tgccaagccc tacgtctttc
601   agtgatagta tcaagcaact tgctgctgag acgctgccaa aatacatgca gcagttgagt
661   agcttggatg cagagacgct gcagaaaaat catgaccagt tcgccacggg cagcggccct
721   cttcgtggca gtatcactca atgccaaggg ctgatgcagt tttgtggtgg ggaattgcaa
781   gctgaggcca gtgccatttt aaacacgcct gtttgtggta ttcccttctc gcagtgggga
841   actgttggtg gggcggccag cgcgtacgtc gccagtggcg ttgatctaac gcaggcagca
901   aatgagatca aagggctggg gcaacagatg cagcaattac tgtcattgat gtgatatgga
961   taaaaacaag ggggtagtgt ttcccccttt ttctatcaat attgcgaata tcttcgtccc
1021  tgatctttca ggggcgaatc gttttttagc atgctcattg ttagaatttc tgacttatct
1081  ctcttctgta ttactactca tactctggaa aatcctgagc atttatatct atggattgat
1141  gcagcactcg ag
```

FIGURE 4

```
1    agggcattgg aattaaaaat atatttatct aaatgatgat gagtttaaat tacatttgcg
61   tattaaaatg aataacgcat tattaacgta ttaccatctg ttcccgctta atttttaaa
121  aaatttaagg taacaatgag tatatatctt atgggaaaag ccaaaaaact aacgaacact
181  ataataattc gattaacatc aatgaaaata cacggctcac ctattattaa aataatacga
241  ctagcattat aagaaaaaat atttttatg tttatagtat aggcgtgtat ttaattagtt
301  cttaatttaa ttaaggaggg aagcatgaac ttatcattaa gcgatcttca tcgtcaggta
361  tctcgattgg tgcagcaaga gagcggtgat tgtaccggga aattaagagg taacgttgct
421  gccaataaag aaactacctt tcaaggtttg accatagcca gtggtgccag agagtcagaa
481  aaagtatttg ctcaaactgt actaagccac gtagcaaata ttgttctaac tcaagaagat
541  accgctaagc tattgcaaag cacggtaaag cataatttga ataattatga attaagaagt
601  gtcggcaatg gtaatagtgt acttgtcagt ttacgtagtg accaaatgac actacaagac
661  gccaaagtgc tgttggaggc tgcattgcga caagagtcgg gagcgagggg gcatgtatca
721  tctcattcac attcagtcct tcacgcaccg ggaaccccgg tgcgtgaagg actgcgttca
781  catctagacc ccagaacacc accgttgcca ccgcgtgaac gaccacacac ttctggccat
841  cacggggctg gcgaagccag agccaccgca ccaagcactg tttctcctta tggcccagaa
901  gcgcgcgcag aactcagcag ccgcctcacc acattgcgca atacgctggc gccagcaacg
961  aatgatccgc gttacttaca agcctgcggc ggtgaaaagc taaaccgatt tagagatatt
1021 caatgctgtc ggcaaaccgc agtacgcgcc gatcttaatg ccaattacat ccaggtcggt
1081 aacactcgta ccatagcgtg ccagtatccg ctacaatctc aacttgaaag ccatttccgt
1141 atgctggcag aaaaccgaac gccagtgttg gctgttttag cgtccagttc tgagatagcc
1201 aatcaaagat tcggtatgcc agattatttc cgccagagtg gtacctatgg cagtatcact
1261 gtagagtcta aaatgactca gcaagttggt ctcggtgacg ggattatggc agatatgtat
1321 actttaacga ttcgtgaagc gggtcaaaaa acaatttctg ttcctgtggt tcatgttggc
1381 aattggcccg atcagaccgc agtcagctct gaagttacca aggcactcgc ttcactggta
1441 gatcaaacag cagaaacaaa acgcaatatg tatgaaagca aggaagttc agcggtagca
1501 gatgactcca aattacggcc ggtaatacat tgccgtgcgg gtgttggccg tactgcgcaa
1561 ctgattggcg caatgtgcat gaatgatagt cgtaatagtc agttaagcgt agaagatatg
1621 gtcagccaaa tgcgagtaca aagaaatggt attatggtac aaaaagatga gcaacttgat
1681 gttctgatta agttggctga aggacaaggg cgaccattat taaatagcta atgtaaatat
1741 ttattcctat gagtaaataa aattactaag agatatacac cactttgcca atcaaagaaa
1801 ctttaaacct caactaaagt aagcaattag ttgaggttta tctgctatag aataattatt
1861 aacaaaaata taaacaacaa aattaaaagt tatgtgtcta cttttacttt atgtaaccaa
1921 acccattaat ggataccgta cgttttctt ttatagaatt aaaccagtaa atgagatgat
1981 gaaggacgat gatcatcgtc
```

FIGURE 5

```
1    atgattgggc caatatcaca aataaacagc ttcggtggct tatcagaaaa agagacccgt
61   tctttaatca gtaatgaaga gcttaaaaat atcataatac agttggaaac tgatatagcg
121  gatggatcct ggttccataa aaattattca cgcctggata tagaagtcat gcccgcatta
181  gtaattcagg cgaacaataa atatccggaa atgaatctta attttgttac atctccccag
241  gacctttcga tagaaataaa aaatgtcata gaaaatggag ttggatcttc ccgcttcata
301  attaacatgg gggagggtgg aatacatttc agtgtaattg attacaaaca tataaatggg
361  aaaacatctc tgatattatt tgaaccagta aactttaata gtatggggcc agcgatactg
421  gcaataagta caaaaacggc cattgaacgt tatcaattac ctgattgcca tttttccatg
481  gtggaaatgg atattcagcg aagctcatct gaatgtggta ttttagtttt ggcactggca
541  aaaaaacttt acaccgagag agatagcctg ttgaaaatac atgaagataa tataaaaggt
601  atattaagtg atagtgaaaa tcctttaccc cacaataagt tggatccgta tctcccggta
661  acttttttaca aacatactca aggtaaaaaa cgtcttaatg aatatttaaa tactaacccg
721  cagggagttg gtactgttgt taacaaaaaa aatgaaacca tctttaatag gtttgataac
781  aataaatcca ttatagatgg aaaggaatta tcagtttcgg tacataaaaa gagaatagct
841  gaatataaaa cacttctcaa agtataa
```

FIGURE 6

```
ATGAAAATCATGGGAACTATGCCACCGTCGATCTCCCTCGCCAAAGCTCATGAGCGCATCAGCCAACATTGGCAAA
ATCCTGTCGGTGAGCTCAATATCGGAGGAAAACGGTATAGAATTATCGATAATCAAGTGCTGCGCTTGAACCCCCA
CAGTGGTTTTTCTCTCTTTCGAGAAGGGGTTGGTAAGATCTTTTCGGGGAAGATGTTTAACTTTTCAATTGCTCGT
AACCTTACTGAGACACTCCATGCAGCCCAGAAAACGACTTCGCAGGAGCTAAGGTCTGATATCCCCAATGCTCTCA
GTAATCTCTTTGGAGCCAAGCCACAGACCGAACTGCCGCTGGGTTGGAAAGGGAAGCCTTTGTCAGGAGCTCCGGA
TCTTGAAGGGATGCGAGTGGCTGAAACCGATAAGTTTGCCGAGGGCGAAAGCCATATTAGTATAATAGAAACTAAG
GATAATCAGCGGTTGGTGGCTAAGATTGAACGCTCCATTGCCGAGGGGCATTTGTTCGCAGAACTGGAGGCTTATA
AACACATCTATAAAACCGCGGGCAAACATCCTAATCTTGCCAATGTCCATGGCATGGCTGTGGTGCCATACGGTAA
CCGTAAGGAGGAAGCATTGCTGATGGATGAGGTGGATGGTTGGCGTTGTTCTGACACACTAAGAAGCCTCGCCGAT
AGCTGGAAGCAAGGAAAGATCAATAGTGAAGCCTACTGGGGAACGATCAAGTTTATTGCCCATCGGCTATTAGATG
TAACCAATCACCTTGCCAAGGCAGGGATAGTACATAACGATATCAAACCCGGTAATGTGGTATTTGACCGCGCTAG
CGGAGAGCCCGTTGTCATTGATCTAGGATTACACTCTCGTTCAGGGGAACAACCTAAGGGGTTTACAGAATCCTTC
AAAGCGCCGGAGCTTGGAGTAGGAAACCTAGGCGCATCAGAAAAGAGCGATGTTTTCTCGTAGTTTCAACCCTTC
TACATGGTATCGAAGGTTTTGAGAAAGATCCGGAGATAAAGCCTAATCAAGGACTGAGATTCATTACCTCAGAACC
AGCGCACGTAATGGATGAGAATGGTTACCCAATCCATCGACCTGGTATAGCTGGAGTCGAGACAGCCTATACACGC
TTCATCACAGACATCCTTGGCGTTTCCGCTGACTCAAGACCTGATTCCAACGAAGCCAGACTCCACGAGTTCTTGA
GCGACGGAACTATTGACGAGGAGTCGGCCAAGCAGATCCTAAAAGATACTCTAACCGGAGAAATGAGCCCATTATC
TACTGATGTAAGGCGGATAACACCCAAGAAGCTTCGGGAGCTCTCTGATTTGCTTAGGACGCATTTGAGTAGTGCA
GCAACTAAGCAATTGGATATGGGGGTGGTTTTGTCGGATCTTGATACCATGTTGGTGACACTCGACAAGGCCGAAC
GCGAGGGGGAGTAGACAAGGATCAGTTGAAGAGTTTTAACAGTTTGATTCTGAAGACTTACAGCGTGATTGAAGA
CTATGTCAAAGGCAGAGAAGGGGATACCAAGAGTTCCAGTGCGGAAGTATCCCCCTATCATCGCAGTAACTTTATG
CTATCGATCGCCGAACCTTCACTGCAGAGGATCCAAAAGCATCTGGACCAGACACACTCTTTTTCTGATATCGGTT
CACTAGTGCGCGCACATAAGCACCTGGAAACGCTTTTAGAGGTCTTAGTCACCTTGTCACCGCAAGGGCAGCCCGT
GTCCTCTGAAACCTACAGCTTCCTGAATCGATTAGCTGAGGCTAAGGTCACCTTGTCGCAGCAATTGGATACTCTC
CAGCAGCAGCAGGAGAGTGCGAAACGGCAACTATCTATTCTGATTAATCGTTCAGGTTCTTGGGCCGATGTTGCTC
GTCAGTCCCTGCAGCGTTTTGACAGTACCCGGCCTGTAGTGAAATTCGGCACTGAGCAGTATACCGCAATTCACCG
TCAGATGATGGCGGCCCATGCAGCCATTACGCTACAGGAGGTATCGGAGTTTACTGATGATATGCGAAACTTTACA
GCGGACTCTATTCCACTACTGATTCGACTTGGACGAAGCAGTTTAATAGATGAGCATTTGGTTGAACAGAGAGAGA
AGTTGCGAGACGTGACGACCATCGCCGAGCGACTGAACCGGTTGGAGCGGGAATGGATGTGA
```

FIGURE 7

DELIVERY OF PROTEINS INTO EUKARYOTIC CELLS WITH RECOMBINANT YERSINIA

FIELD OF INVENTION

The present invention relates to recombinant Yersinia and the use thereof for delivery of proteins into eukaryotic cells.

BACKGROUND

Bacteria of the genus Yersinia cause diseases in humans and rodents ranging from enteritis and lymphadenitis to plague. The genus Yersinia encompasses three species: *Yersinia enterocolitica,* which is the most prevalent Yersinia species in humans and causes a broad range of gastrointestinal syndromes; *Yersinia pseudotuberculosis,* which causes adenitis and septicaemia; and *Yersinia pestis,* which is the causative agent of plague.

In spite of the differences in the infection routes, these three species of Yersinia share a common capacity to resist the non-specific immune response of the human or rodent host and to proliferate in the host lymphatic tissues. Anatomo-pathological examinations revealed that Yersinia are not detected inside the inflammatory or parenchymal cells of the infected animals (Simonet et al. (1990) *Infect. Immun.* 58: 841–845). Consistent with these in vivo observations, Yersinia are resistant to phagocytosis in vitro by macrophages and polymorphonuclear leukocytes. See review by Cornelis et al. (1997) *Mol. Microbiol.* 23(5): 861–867. *Yersinia enterocolitica* also has the capacity to enter certain cultured epithelial cells, a process generally referred to as invasion (Miller et al. (1988) *Infect. Immun.* 56: 1242–1248).

Genetic studies revealed that the virulence of Yersinia is determined by a 70 kb plasmid (pYV), which encodes and governs the production of a set of proteins called Yops (for Yersinia outer proteins). These Yops form an integrated anti-host system that allows the extracellular adhesion of Yersinia to the surface of host cells and the subsequent injection of a set of toxic effector proteins into the host cell's cytosol. Recent studies further revealed that such an anti-host system, also called "Yersinia virulon", is composed of the following four elements: (i) a contact or type III secretion system called Ysc, which is devoted to the secretion of Yop proteins out of the bacterial cells; (ii) a set of "translocators" for translocating the effector proteins into the eukaryotic host cells, which consist of YopB, YopD and possible other proteins such as LcrV; (iii) a control element and recognition system (YopN and LcrG); and (iv) a set of "effector proteins" including YopE, YopH, YopO/YpkA, YopM and YopP/YopJ, which are injected (or translocated) into the eukaryotic host cells and disrupt the functions of such host cells. Transcription of these genes is controlled both by temperature and by contact with a eukaryotic cell. See review by Cornelis et al. (1997).

The effector proteins disrupt the function of host cells in a number of ways. The 23 kd YopE is a cytotoxin that disrupts the actin-microfilament structure of cultured Hela cells (Rosqvist et al. (1990) *Mol. Microbiol.* 4: 657–667; Rosqvist et al. (1991) *Infect. Immun.* 59: 4562–4569). The 51 kd YopH is a protein tyrosine phosphatase (PTPase) related to eukaryotic PTPases, which acts on tyrosinephosphorylated proteins of infected macrophages (Hartland et al. (1994) *Infect. Immun.* 62: 4445–4453). Presumably as a result of this action, YopH inhibits bacterial uptake and oxidative burst by cultured macrophages (Rosquvist et al. (1988) *Infect. Immun.* 56: 2139–2143; Bliska et al. (1995) *Infect. Immun.* 63: 681–685). YopO (or YpkA) is an 81 kd serine/threonine kinase, which is targeted to the inner surface of the plasma membrane of the eukaryotic cell and might function to interfere with the signal transduction pathway of the eukaryotic cell (Hakansson et al. (1996) *Mol. Microbiol.* 20: 593–603). YopM is an acidic 41 kd protein having 12 leucine-rich repeats, which suggests that YopM might bind thrombin and interfere with platelet-mediated events of the inflammatory response (Leung et al. (1989) *J. Bacterial.* 171: 4623–4632). YopP is involved in the induction of apoptosis in macrophages (Mills et al. (1997) Proc. Acad. Natl. Sci. USA 94: 12638–12643).

The molecular structures of these effector proteins have been investigated to determine the elements in each effector protein that are required for their secretion and translocation. For this purpose, hybrid proteins have been engineered by fusing truncated Yop effector proteins of different length with certain reporter enzymes such as the calmodulin-activated adenylate cyclase domain (or Cya) of the *Bordetella pertussis* cyclolysin. Successful secretion and/or translocation events could be detected by assays based on the enzymatic activity of the reporter protein. Sory et al. disclose, by applying this approach, that YopE and YopH of *Y. enterocolitica* are modular proteins composed of three domains, i.e., an N-terminal domain required for secretion, a translocation domain required for translocation into cells, and a C-terminal catalytic domain responsible for the toxic effector activity. Sory et al. (1995) *Proc. Natl. Acad. Sci. USA* 92: 11998–12002. The same domain organization has been demonstrated for YopM of *Y. enterocolitca* (Boland et al. (1996) *EMBO J.* 15: 5191–5201).

The present invention provides recombinant Yersinia for safe delivery of proteins into eukaryotic cells. Such Yersinia are deficient in the production of functional effector proteins, but are endowed with a functional secretion and translocation system. The present invention further provides expression vectors for use in combination with such mutant Yersinia for safe and efficient delivery of desired proteins into eukaryotic cells. This approach is useful not only for studying the function of a given protein, but also for designing therapeutic approaches. For example, a protein of a pathogenic origin, e.g., a tumor associated protein, a parasite antigen, or a viral antigen, can be delivered using the recombinant Yersinia of the present invention into antigen presenting cells for inducing an immune response specific for such a protein.

Most progressively growing neoplastic cells express potentially immunogenic tumor-associated antigens (TAAs), also called tumor rejection antigens (TRAs). TRAs, like other antigenic epitopes, are presented at the surface of tumor cells by MHC molecules and have been shown to induce a CTL response in vivo and in vitro. See, for example, van der Bruggen et al. (1991) *Science* 254: 1643–1647. However, such TRA-expressing tumor cells do not provoke reliable anti-tumor immune responses in vivo that are capable of controlling the growth of malignant cells. Boon et al. (1992) *Cancer Surveys* 13: 23–37; T. Boon (1993) *Int. J. Cancer* 54: 177–180; T. Boon (1992) *Advances Cancer Res.* 58: 177–209.

A number of genes have been identified that encode tumor rejection antigen precursors (or TRAPs), which are processed into TRAs in tumor cells. Such TRAP-encoding genes include members of the MAGE family, the BAGE family, the DAGE/Prame family, the GAGE family, the RAGE family, the SMAGE family, NAG, Tyrosinase, Melan-A/MART-1, gp100, MUC-1, TAG-72, CA125, mutated proto-oncogenes such as p21ras, mutated tumor suppressor genes such as p53, tumor associated viral antigens such as HPV16 E7. See, e.g., review by Van den Eynde and van der Bruggen (1997) in *Curr. Opin. Immunol.* 9:684–693, Sahin et al. (1997) in *Curr. Opin. Immunol.* 9:709–716, and Shawler et al. (1997) *Advances in Pharmacology* 40: 309–337 Academic Press, Inc.: San Diego, Calif. The identification of these genes has allowed recombinant production of TRAs or TRAPs which may be subsequently used as vaccines to treat various cancerous conditions.

The present invention contemplates the use of recombinant Yersinia for delivery of desired proteins into eukaryotic cells. Particularly, the recombinant Yersinia of the present invention are useful for delivery of proteins or derivatives thereof to antigen presenting cells. In accordance with the present invention, antigen presenting cells upon receiving the delivery, present antigenic epitopes which can be recognized by T cells. Thus, the recombinant Yersinia of the present invention can be employed in a number of immune diagnostic or therapeutic approaches.

The present invention is further elaborated upon the following disclosure.

SUMMARY OF THE INVENTION

The present invention relates to recombinant Yersinia and the use thereof for delivery of proteins into eukaryotic cells.

One embodiment of the present invention provides mutant Yersinia strains deficient in producing functional effector proteins. A preferred mutant Yersinia strain of the present invention is a quintuple-mutant strain designated as yopE-HMOP.

Another embodiment of the present invention provides expression vectors for delivery of heterologous proteins to eukaryotic cells. In accordance with the present invention, such an expression vector is characterized by (in the 5' to 3' direction) a promoter, a first nucleic acid sequence encoding a delivery signal, a second nucleic acid sequence fused thereto coding for a heterologous protein to be delivered.

According to this embodiment of the present invention, the promoter is preferably one from a Yersinia virulon gene; more preferably, an effector-encoding gene; even more preferably, a YopE gene. The delivery signal is a polypeptide sequence from an Yersinia effector, including YopE, YopH, YopO/YpkA, YopM, and YopP/YopJ. Such delivery signal can be recognized by the secretion and translocation system of Yersinia. The heterologous protein of the present invention includes naturally occurring proteins or parts thereof such as tumor-associated proteins or known antigens of pathogens. The heterologous protein of the present invention also includes artificially designed proteins such as in-frame fusion of proteins or parts of proteins.

Yet another embodiment of the present invention provides recombinant Yersinia, i.e., yersinia of the above-described mutant strains further transformed with the expression vector of the present invention. Such recombinant Yersinia is preferred for delivery of heterologous proteins into eukaryotic cells. A preferred eukaryotic cell is an antigen presenting cell capable of presenting immunogenic epitopes derived from the heterologous proteins being delivered.

In a further aspect of the present invention, such recombinant Yersinia are contemplated in immunogenic compositions and methods for inducing an immune response, either a cellular immune response or a humoral immune response, or a combination of both.

Further to this aspect of the invention, the recombinant Yersinia of the present invention can be employed in an in vitro regime for assessing the efficacy of a vaccination regimen. The recombinant Yersinia of the present invention can also be employed in an ex vivo regime to generate specific CTLs and to use such CTLs for treating various pathological conditions such as tumors or infections by pathogens. The recombinant Yersinia of the present invention can also be employed in an in vivo regime, i.e., as a recombinant vaccine, to treat subjects suffering pathological conditions such as tumors or infections by pathogens.

BRIEF DESCRIPTION OF FIGURES

FIG. 2(A)–(B) depicts the procedure for stimulating CTL 82/30 with EBV-transformed human B cells (HLA-A1) mixed with recombinant Yersinia; (B) depicts the quantitation of IFN-γ released by activated CTLs.

FIG. 3 depicts the sequence of the *Yersinia enterocolitica* YopM gene (SEQ ID NO:33).

FIG. 4 depicts the sequence of the *Yersinia enterocolitica* YopE gene (SEQ ID NO:34).

FIG. 5 depicts the sequence of the *Yersinia enterocolitica* YopH gene (SEQ ID NO:35).

FIG. 6 depicts the sequence of the *Yersinia enterocolitica* YopP gene (SEQ ID NO:36).

FIG. 7 depicts the sequence of the *Yersinia enterocolitica* YopP gene (SEQ ID NO:37).

DETAILED DESCRIPTION OF THE INVENTION

The present invention relates to recombinant Yersinia and the use thereof for delivery of proteins into eukaryotic cells.

In particular, the present invention provides mutant Yersinia strains that are deficient in producing functional effector proteins. The present invention further provides an expression vector, which, when transformed into a Yersinia of the above-described mutant strains, permits delivery of a desired protein, e.g., a MAGE-1 protein, into a eukaryotic cell, for example, a EBV-transformed human B cell. The present invention provides that, upon receiving the delivered protein, the antigen presenting cell processes the delivered protein and presents antigenic epitopes in the context of an MHC molecule leading to an immune response specific for the protein being delivered. For example, human B cells after taking up the MAGE-1 protein from a recombinant Yersinia of the present invention are recognized by a CTL clone specific for a MAGE-1 epitope. Thus the present invention provides an effective recombinant Yersinia system with diminished toxicity for delivery of desired proteins into eukaryotic cells.

The term "Yersinia" as used herein means all species of Yersinia, including *Yersinia enterocolitica, Yersinia pseudotuberculosis* and *Yersinia pestis.*

For the purpose of the present invention, the term "recombinant Yersinia" used herein refers to Yersinia genetically transformed with the expression vectors of the present invention.

The term "delivery" used herein refers to the transportation of a protein from a Yersinia to a eukaryotic cell, including the steps of expressing the protein in the Yersinia, secreting the expressed protein(s) from such Yersinia and translocating the secreted protein(s) by such Yersinia into the cytosol of the eukaryotic cell. Accordingly, a "delivery signal" refers to a polypeptide sequence which can be recognized by the secretion and translocation system of Yersinia and directs the delivery of a protein from Yersinia to eukaryotic cells.

Figure 1:
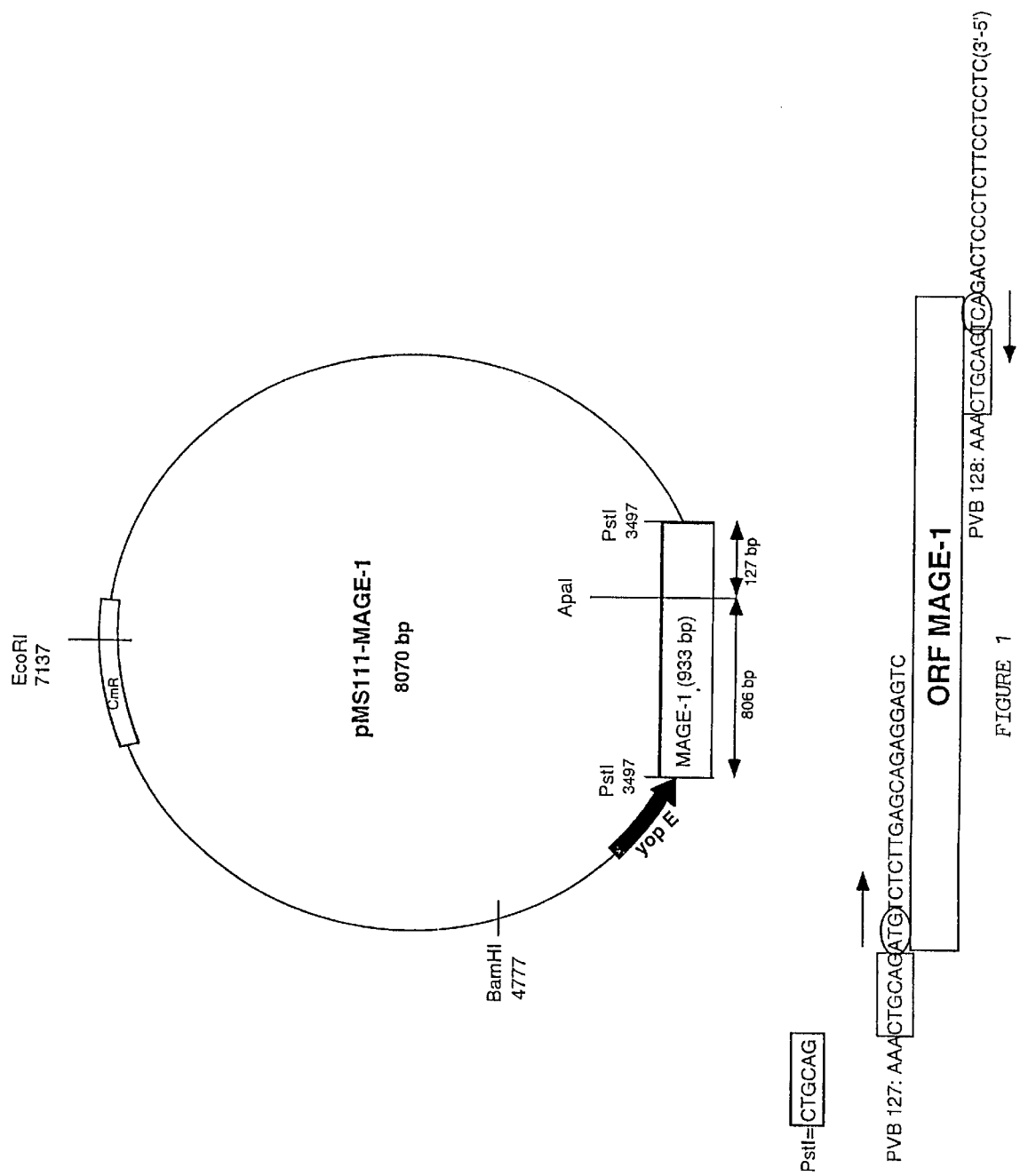
FIG. 1 illustrates the plasmid map of the expression vector pMS111-MAGE-1 (YopE$_{130}$-MAGE1). Primers are SEQ ID NOS:38 and 39.

As used herein, the "secretion" of a protein refers to the transportation of such protein outward across the cell membrane of a Yersinia. The "translocation" of a protein refers to the transportation of such protein across the plasma membrane of a eukaryotic cell into the cytosol of such eukaryotic cell.

"Eukaryotic cells" as used herein, the surface of which Yersinia adhere to, are also referred to as "target cells" or "target eukaryotic cells".

One embodiment of the present invention provides mutant Yersinia strains which are deficient in producing functional effector proteins.

The effector proteins of Yersinia, i.e., the Yersinia virulon proteins which are normally translocated into the cytosol of the target eukaryotic cells, are toxic to the target cell. Thus, a "functional effector protein" refers to an effector protein having a defined catalytic activity and which is capable of eliciting specific toxicity toward the target cells.

Accordingly, the mutant Yersinia of the present invention are used for delivery of proteins to eukaryotic cells, with diminished toxicity, i.e., toxicity which does not completely disable or kill the target cell. For the purpose of delivering proteins, the secretion and translocation system of the instant mutant Yersinia need to be intact.

Five effector genes have been cloned from *Y. enterocolitica* which are YopE, YopH, YopO, YopM, and YopP (FIGS. 3–7). The equivalent effector genes have been cloned from *Y. pseudotuberculosis* and are named as YopE, YopH, YpkA, YopM, and YopJ, respectively. Some effector genes have also been cloned from *Y. pestis*. The nucleic acid sequences of these Yop genes are available to those skilled in the art, e.g., in the Genebank Database For the purpose of the present invention, the effector-encoding genes are denoted by italicized letters to be distinguished from the effector proteins. Mutant effector genes are denoted by letters of lower case. For example, YopE refers to the effector protein encoded by the YopE gene. YopE represents the wild type gene, while yopE represents a gene having a mutation.

According to the present invention, a mutant Yersinia strain can be generated by introducing at least one mutation into at least one effector-encoding gene. Preferably, such effector-encoding genes include YopE, YopH, YopO/YpkA, YopM, and YopP/YopJ. The skilled artisan may employ any number of standard techniques to generate mutations in these Yop genes. Sambrook et al. describe in general such techniques. See Sambrook et al. (1989) *Molecular Cloning: A Laboratory Manual, Second Edition* Cold Spring Harbor Laboratory Press: Cold Spring Harbor, N.Y.

The term "mutation" is used herein as a general term and includes changes of both single base pair and multiple base pairs. Such mutations may include substitutions, frame-shift mutations, deletions and truncations.

In accordance with the present invention, the mutation can be generated in the promoter region of an effector-encoding gene so that the expression of such effector gene is abolished.

The mutation can also be generated in the coding region of an effector-encoding gene such that the catalytic activity of the encoded effector protein is abolished. The "catalytic activity" of an effector protein refers to the anti-target cell function of an effector protein, i.e., toxicity. Such activity is governed by the catalytic motifs in the catalytic domain of an effector protein. The approaches for identifying the catalytic domain and/or the catalytic motifs of an effector protein are well within the ken of those skilled in the art. See, for example, Sory et al. (1995), Boland et al. (1996) and Cornelis et al. (1997).

Accordingly, one preferred mutation of the present invention is a deletion of the entire catalytic domain. Another preferred mutation is a frameshift mutation in an effector-encoding gene such that the catalytic domain is not present in the protein product expressed from such "frameshifted" gene. A most preferred mutation is a mutation with the deletion of the entire coding region.

Other mutations are also contemplated by the present invention, such as small deletions or base pair substitutions, which are generated in the catalytic motifs of an effector protein leading to destruction of the catalytic activity of a given effector protein.

The mutations that are generated in the Yop genes may be introduced into Yersinia by a number of methods. One such method involves cloning a mutated Yop gene (i.e., a yop gene), into a "suicide" vector which is capable of introducing the mutated yop sequence into Yersinia via allelic exchange. Such "suicide" vectors are described by Kaniga et al. (1991) *Gene* 109: 137–141 and by Sarker et al. (1997) *Mol. Microbiol* 23: 409–411.

In this manner, mutations generated in multiple Yop genes may be introduced successively into Yersinia, giving rise to polymutant recombinant Yersinia. The order in which these mutated yop sequences are introduced is not important.

A preferred mutant Yersinia strain of the present invention is a quintuple-mutant Yersinia strain in which all the effector-encoding genes are mutated such that the resulting Yersinia no longer produce any functional effector proteins. Such quintuple-mutant Yersinia strain is designated as yopE-HOMP for *Y. enterocolitica* or yopEHAMJ for *Y. pseudotuberculosis*. One example of such yopEHOMP strain is *Y. enterocolitica* MRS40(pABL403).

Under some circumstances, it may be desired to mutate only some but not all of the effector Yop genes. For example, when a delivery is intended to target a macrophage, YopH is preferably not mutated since YopH is understood to inhibit the phagocytosis by macrophages. Rosqvist et al. (1988) and Rosqvist et al. (1989). Accordingly, the present invention further contemplates polymutant Yersinia other than quintuple-mutant Yersinia, e.g., double-mutant, triple-mutant, and quadruple-mutant Yersinia.

Alternatively, the quintuple-mutant strain yopEHOMP may still be used for delivery to macrophages, in which case a wild type YopH gene can be introduced into the quintuple-mutant *Y.* yopEHOMP strain by various known transformation procedures which are further described hereinafter. In this manner, a polymutant Yersinia strain can be generated in which a desired set of Yop genes are mutated such that only the protein of interest is delivered into the target cells.

A further aspect of the present invention is directed to an expression vector for use in combination with the instant mutant Yersinia strains to deliver a desired protein into eukaryotic cells. In accordance with the present invention, such a vector is characterized by (in the 5' to 3' direction) a promoter, a first nucleic acid sequence encoding a delivery signal, a second nucleic acid sequence fused thereto coding for a heterologous protein to be delivered.

In accordance with present invention, the promoter of the expression vector is preferably from a Yersinia virulon gene. A "Yersinia virulon gene" refers to genes on the Yersinia pYV plasmid, the expression of which is controlled both by temperature and by contact with a target cell. See review by Cornelis et al. (1997). Such genes include genes coding for elements of the secretion machinary (the Ysc genes), genes coding for translocators (YopB, YopD, and LcrV), genes coding for the control elements (YopN and LcrG), and genes coding for effectors (YopE, YopH, YopO/YpkA, YopM and YopP/YopJ).

In a preferred embodiment of the present invention, the promoter is from an effector-encoding gene selected from any one of YopE, YopH, YopO/YpkA, YopM and YopP/YopJ. More preferrably, the promoter is from YopE.

Further in accordance with the present invention, a first DNA sequence coding for a delivery signal is operably linked to the promoter.

"A delivery signal", as described hereinabove, refers to a polypeptide which can be recognized by the secretion and translocation system of Yersinia and therefore directs the secretion and translocation of a protein into a eukaryotic cell.

According to the present invention, such a polypeptide is from an effector protein. The effector proteins include YopE, YopH, YopO/YpkA, YopM, and YopP/YopJ. Preferably, the effector protein is YopE. More preferably, the effector protein is YopE of Yersinia enterocolitica.

One skilled in the art is familiar with the methods for identifying the polypeptide sequences of an effector protein that are capable of delivering a protein. For example, one such method is described by Sory et al. (1994). Briefly, polypeptide sequences from various portions of the Yop proteins can be fused in-frame to a reporter enzyme such as the calmodulin-activated adenylate cyclase domain (or Cya) of the Bordetella pertussis cyclolysin. Delivery of a Yop-Cya hybrid protein into the cytosol of eukaryotic cells is indicated by the appearance of cyclase activity in the infected eukaryotic cells that leads to the accumulation of cAMP. Examples of such delivery signal polypeptides include from *Y. enterocolitica:* $YopE_{130}$ (the N-terminal 130 amino acids of YopE), $YopE_{50}$, $YopM_{100}$ and $YopH_{71}$.

By employing such an approach, one skilled in the art can determine, if desired, the minimal sequence requirement, i.e., a contiguous amino acid sequence of the shortest length, that is capable of delivering a protein. See, e.g., Sory et al (1994). Accordingly, preferred delivery signals of the present invention consists of at least the minimal sequence of amino acids of a Yop effector protein that is capable of delivering a protein.

Further in accordance with the present invention, a second DNA sequence encoding a heterologous protein is fused in frame to the first DNA sequence in the instant vector for delivery into eukaryotic cells.

The term "heterologous protein" used herein refers to a protein other than a Yersinia Yop protein. "Yop proteins" refer to Yersinia virulon proteins that are secreted, including the translocators and the effectors.

According to the present invention, "a heterologous protein" includes naturally occuring proteins or parts thereof. The term "part of a protein" includes a peptide or polypeptide fragment of a protein that is of sufficient length to be antigenic. Preferably, such a fragment consists of at least 8 or 9 contiguous amino acids of a protein. "A heterologous protein" as used in the present invention also includes artificially engineered proteins or parts thereof, such as fusion of two or more naturally occurring proteins or parts thereof, polypeptides (in-frame fusion of two or more peptide epitopes) as exemplified by Thompson et al. (1995) in *Proc. Natl. Acad. Sci. USA* 92: 5845–5849.

The protein expressed from the fused first and second DNA sequences is also termed as a "fusion protein" or a "hybrid protein", i.e., a hybrid of Yersinia delivery signal and a heterologous protein.

There is no particular limitation in the heterologous protein that can be delivered. The present invention particularly contemplates proteins, such as, e.g., known tumor associated proteins, known antigens of pathogens, and cytokines.

A "tumor associated protein" refers to a protein that is specifically expressed in tumors or expressed at an abnormal level in tumors relative to normal tissues. Such tumor associated proteins include, but are not limited to, members of the MAGE family, the BAGE family (such as BAGE-1), the DAGE/Prame family (such as DAGE-1), the GAGE family, the RAGE family (such as RAGE-1), the SMAGE family, NAG, Tyrosinase, Melan-A/MART-1, gp100, MUC-1, TAG-72, CA125, mutated proto-oncogenes such as p21ras, mutated tumor suppressor genes such as p53, tumor associated viral antigens (e.g., HPV16 E7), HOM-MEL-40, HOM-MEL-55, NY-COL-2, HOM-HD-397, HOM-RCC-1.14, HOM-HD-21, HOM-NSCLC-11, HOM-MEL-2.4, and HOM-TES-11. Members of the MAGE family include, but are not limited to, MAGE-1, MAGE-2, MAGE-11. Members of the GAGE family include, but are not limited to, GAGE-1, GAGE-6. See, e.g., review by Van den Eynde and van der Bruggen (1997) in *Curr. Opin. Immunol.* 9:684–693, Sahin et al. (1997) in *Curr. Opin. Immunol.* 9:709–716, and Shawler et al. (1997). These proteins have been shown to associate with certain tumors such as melanoma, lung cancer, prostate cancer, breast cancer, renal cancer and others.

A number of known antigens derived from pathogens can also be employed according to the present invention. Pathogens contemplated by the present invention include viruses, bacteria, parasites and fungi. Specific examples of antigens characteristic of a pathogen include the influenza virus nucleoprotein (residues 218–226, as set forth in F. et al. (1997) *J. Virol.* 71: 2715–2721) antigens from Sendai virus and lymphocytic choriomeningitis virus (see, An et al. (1997) *J. Virol.* 71: 2292–2302), the B1 protein of hepatitis C virus (Bruna-Romero et al. (1997) *Hepatology* 25: 470–477), the virus envelope glycoprotein gp 160 of HIV (Achour et al. (1996) *J. Virol.* 70: 6741–6750), amino acids 252–260 or the circumsporozite protein of *Plasmodium berghei* (Allsopp et al. (1996) *Eur. J. Immunol.* 26: 1951–1958), the influenza A virus nucleoprotein (residues 366–374, Nomura et al. (1996) *J. Immunol. Methods* 193: 4149), the listeriolysin O protein of *Listeria monocytogenes* (residues 91–99, An et al. (1996) *Infect. Immun.* 64: 1685–1693), the E6 protein (residues 131–140, Gao et al. (1995) *J. Immunol.* 155: 5519–5526) and E7 protein (residues 21–28 and 48–55, Bauer et al. (1995) *Scand. J. Immunol.* 42: 317–323) of human papillomavirus type 16, the M2 protein of respiratory syncytial virus (residues 82–90 and 81–95, Hsu et al. (1995) *Immunology* 85: 347–350), the herpes simplex virus type 1 ribonucleotide reductase (see, Salvucci et al. (1995) *J. Gen. Virol.* 69: 1122–1131) and the rotavirus VP7 protein (see, Franco et al. (1993) *J. Gen. Virol.* 74: 2579–2586), *P. falciparum* antigens (causing malaria) and hepatitis B surface antigen (Gilbert et al. (1997) *Nature Biotech.* 15: 1280–1283).

Accordingly, sequences coding for the above-described proteins may be cloned into the present expression vector for delivery.

A number of coding sequences for small antigenic peptides can also be employed in the present invention. One skilled in the art can readily determine the length of the fragments required to produce immunogenic peptides. Alternatively, the skilled artisan can also use coding sequences for peptides that are known to elicit specific T cell responses, such as tumor-associated antigenic peptides (TRAs) as disclosed by U.S. Pat. No. 5,462,871, U.S. Pat. No. 5,558,995, U.S. Pat. No. 5,554,724, U.S. Pat. No. 5,585,461, U.S. Pat. No. 5,591,430, U.S. Pat. No. 5,554,506, U.S. Pat. No. 5,487,974, U.S. Pat. No. 5,530,096, U.S. Pat. No. 5,519,117. Examples of TRAs are provided in Table 1. See also review by Van den Eynde and van der Bruggen (1997) and Shawler et al. (1997). Antigenic peptides of a pathogen origin can also be used, such as those disclosed by Gilbert et al. (1997).

As described herein above, sequences coding for a full-length naturally occurring protein, a part of a naturally occurring protein, combinations of parts of a naturally occurring protein, or combinations of different naturally occurring proteins or parts from different proteins, may all be employed in the present invention. For example, a sequence coding for multiple epitopes may be used, such as those described by Thomson et al. (1995). Preferably, the second DNA sequence of the present expression vector codes for at least one epitope of a protein. An "epitope" refers to a peptide of at least 8 or 9 amino acids.

Those skilled in the art are familiar with the techniques to make DNA fragments coding for a part of a protein, or link a DNA sequence encoding a part of one protein in frame to a DNA sequence encoding a part of another protein and the like.

The vectors of the instant invention may include other sequence elements such as a 3' termination sequence (including a stop codon and a poly A sequence), or a gene conferring a drug resistance which allows the selection of Yersinia transformants having received the instant vector.

The expression vectors of the present invention may be transformed by a number of known methods into Yersinia. For the purpose of the present invention, the methods of transformation for introducing an expression vector include, but are not limited to, electroporation, calcium phosphate mediated transformation, conjugation, or combinations thereof. For example, a vector can be transformed into a first bacteria strain by a standard electroporation procedure. Subsequently, such a vector can be transferred from the first bacteria strain into Yersinia by conjugation, a process also called "mobilization". Yersinia transformant (i.e., Yersinia having taken up the vector) may be selected, e.g., with antibiotics. These techniques are well known in the art. See, for example, Sory et al. (1994).

One preferred embodiment of the present invention is directed to a Yersinia of the above-described mutant Yersinia strain transformed with an expression vector for delivery of a heterologous protein as herinabove described into a eukaryotic cell.

Accordingly, the present invention contemplates a method for delivering heterologous proteins as hereinabove described into eukaryotic cells.

The present invention contemplates a wide range of eukaryotic cells that may be targeted by the instant recombinant Yersinia.

By "target", is meant the extracellular adhesion of Yersinia to a eukaryotic cell.

In particular, the present invention contemplates antigen-presenting cells. "Antigen presenting cells" as referred herein express at least one class I or class II MHC determinant and may include those cells which are known as professional antigen-presenting cells such as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used according to the present invention. Examples of facultative antigen-presenting cells include astrocytes, follicular cells, endothelium and fibroblasts. As used herein, "antigen-presenting cells" encompass both professional and facultative types of antigen-presenting cells.

The antigen presenting cells can be isolated from tissue or blood (containing peripheral blood mononuclear cells) samples obtained from a mammal such as a human or rodent. Cell lines established from such samples may also be used. Procedures for establishing cell lines are well known in the art. Certain cell lines may be obtained directly from the American Type Culture Collection, 10801 University Boulevard, Manassas, Va. 20110-2209. Both normal and malignant cells may be employed.

In accordance with a preferred embodiment of the present invention, the MHC determinants expressed by the antigen presenting cell are compatible with those expressed by the mammal involved, and at least one of these MHC determinants is capable of presenting one or more antigenic epitopes derived from the protein being delivered.

One skilled in the art is also familiar with the methods for determining whether the MHC molecules expressed by the antigen presenting cell are compatible with those of the mammal subject involved, such as well known HLA-typing procedures. See general teachings by Coligan et al. (1994) *Current Protocols in Immunology* John Wiley & Sons Inc: New York, N.Y.

Those skilled in the art are able, through the extensive teachings in the art, to determine the MHC molecule for presentation of a particular antigen. For example, U.S. Pat. No. 5,405,940 teaches the determination of HLA-A1 as the presenting molecule for a peptide of MAGE-1, EADPT-GHSY; U.S. Pat. No. 5,558,995 teaches the determination of HLA-Cw1601 for presenting another peptide of MAGE-1, SAYGEPRKL; U.S. Pat. No. 5,530,096 teaches the determination of HLA-A2 as the presenting molecule for a peptide of Tyrosinase, MLLAVLYCL. In the event the eukaryotic cells being targeted do not express a desired HLA or MHC molecule, the gene encoding such molecule may be introduced into the eukaryotic cells by well known transformation or transfection procedures.

Further in accordance with the present invention, the delivery of a protein can be achieved by contacting a eukaryotic cell with a recombinant Yersinia under appropriate conditions. Various references and techniques are conventionally available for those skilled in the art regarding the conditions for inducing the expression and translocation of virulon genes, including the desired temperature, Ca++ concentration, manners in which Yersinia and target cells are mixed, and the like. See, for example, Cornelis, *Cross talk between Yersinia and eukaryotic cells,* Society for General Microbiology Symposium, 55; MoCRAE, SAUNDERS, SMYTH, STOW (eds), *Molecular aspects of host-pathoge interactions,* Cambridge University Press, 1997. The conditions may vary depending on the type of eukaryotic cells to be targeted, e.g., the conditions for targeting human epithelial carcinoma Hela cells (Sory et al. (1994)); the conditions for targeting mouse thymoma or melanoma cells (Starnbach et al. (1994) *J. Immunol.* 153: 1603);.the conditions for targeting mouse macrophages (Boland et al. (1996)). Such variations can be addressed by those skilled in the art using conventional techniques.

Those skilled in the art can also use a number of assays to determine whether the delivery of a fusion protein is successful. For example, the fusion protein may be labeled with an isotope or an immunofluoresceine, or detected by a immunofluoresceine conjugated antibody, as disclosed by Rosqvist et al. (1994) *EMBO J.* 13: 964. The determination can also be based on the enzymatic activity of the protein being delivered, e.g., the assay described by Sory et al. (1994). The determination can also be based on the antigenicity of the protein being delivered. For example, the delivery of a MAGE-1 protein into EBV-transformed human B cells can be detected by the recognition of such targeted B cells by CTL cells specific for MAGE-1 epitopes. Such CTL recognition, in turn, may be detected by a number of assays including assaying the secretion of IFN-γ from the activated CTLs or $Cr^{51}$ release from lysed target cells. Methods such as Western-blot analysis using antibodies specific against the protein being delivered, PCR in situ hybridization, or ELISPOT (Mabtech AB, Sweden) may also be employed for such determination. See, e.g., W. Herr et al. (1997) *J. Immunol. Methods* 203: 141–152 and W. Herr et al. (1996) *J. Immunol. Methods* 191: 131–142.

In a further aspect of the present invention, recombinant Yersinia capable of delivering proteins to antigen-presenting cells are employed for inducing an immune response. Accordingly, the present invention contemplates immunogenic compositions and methods for inducing specific immune responses using the instant recombinant Yersinia as described hereinabove.

The immune responses contemplated by the present invention include cellular immune responses (mediated primarily by T cells) and humoral immune responses (mediated primarily by antibodies). Janeway and Travers teach in general these immune response. (Janeway and Travers (1996) *Immunology, The Immune System in Health and Disease* 2nd ed. Garland Publishing, Inc.: New York, N.Y., and London, England.) (See also, review by O. Tureci et al. (1997) *Molecular Medicine Today* 3(8): 342–349.

According to this aspect of the present invention, the immune responses induced with recombinant Yersinia can be utilized in a number of regimes for diagnostic or therapeutic use. For example, recombinant Yersinia can be employed in an in vitro procedure for monitoring the efficacy of a vaccination therapy in a mammal such as a human or rodent. In this regime, certain antigen presenting cells (e.g., dendritic cells) are taken from a subject being vaccinated with immunogenic compositions, e.g., a particular antigen. Such antigen presenting cells are then contacted with recombinant Yersinia capable of delivering the antigen which is used for vaccination. Subsequently, peripheral blood lymphocytes taken from the same subject (i.e., autologous PBLs) are added, preferably in combination with cytokines such as IL-2, to the mixture of antigen presenting cells and Yersinia. The efficacy of the vaccination can be assessed after priming and then after successive boosts by the presence of CTLs or antibodies that are specific for the relevant antigen. The presence of specific CTLs can be detected using standard assays such as an assay for $Cr^{51}$ release or for the secretion of IFN-gamma. The presence of specific antibodies can be detected by assays such as ELISA using the antigens which are immobilized on a culture plate, or a standard proliferation assay for T-helper cells.

Recombinant Yersinia can also be employed in an ex vivo regime for inducing CTLs specific for a protein. The procedure to develop such specific CTLs in vitro is known in the art, e.g., as disclosed by the U.S. Pat. No. 5,342,774. Briefly, a blood sample containing T cell precursors is taken from a mammal. PBLs are purified from such blood sample and are incubated with stimulator cells expressing an antigenic epitope in the context of an MHC molecule. CTLs specific for such epitope produced can be detected by assays such as an assay for $Cr^{51}$ release or secretion of IFN-gamma.

According to the present invention, a mixture of a recombinant Yersinia and an antigen presenting cell can be used as the "stimulator cell" in such an in vitro procedure for producing CTLs specific for the protein being delivered. The MHC determinants expressed by the antigen presenting cell used are compatible with those expressed by the mammal from which PBLs are isolated, and at least one of these MHC molecules is capable of presenting, to T cells, one or more epitopes derived from the protein being delivered. CTL cells generated as such can be administered, in a therapy regimen of adoptive transfer, to a mammal a pathological condition characterized by an abnormal expression of the protein used in the delivery system. See teachings by Greenberg (1986) *J. Immunol.* 136 (5): 1917; Riddel et al. (1992) *Science* 257: 238; Lynch et al. (1991) *Eur. J. Immunol.* 21: 1403; and Kast et al. (1989) *Cell* 59: 603 for adoptive transfer. CTLs, by lysing the cells abnormally expressing such antigens, can alleviate or treat the pathological condition at issue such as a tumor, an infection with a parasite or a virus.

Accordingly, the present invention contemplates methods and compositions for treating pathological conditions. The pathological conditions contemplated by the present invention include tumors and infections by pathogens such as bacteria, parasites, fungus or virus.

By "treating", is meant alleviating or inhibiting a pathological condition, e.g., inhibiting tumor growth or metastasis, reducing the size of tumor, or diminishing symptoms of a pathogen infection.

The recombinant Yersinia of the present invention can also be employed in vivo, i.e., introducing recombinant Yersinia into a mammal, such as a human or rodent subject.

For in vivo use of recombinant Yersinia, the safety can be tested in animals beforehand. In this case, the recombinant Yersinia may be administered to the animal orally or directly into the stomach. The animals may be sacrificed a few days (1–3 days) after the administration of the recombinant Yersinia. The intestines are washed and the Peyer patches or the faeces can be examined for viable Yersinia. See, e.g., Sory et al. (1992) *Infect. Immun.* 60: 3830–3836. The recombinant Yersinia may also be administered to the animal by intraperitoneal injection. Organs of sacrificed animals such as spleen and liver can be examined for the presence of intracellular Yersinia, an indication of insufficient safety. Intracellular Yersinia may be detected by e.g., cultivating cell extracts on solid medium. See teachings by Sory et al. (1988) *Microb. Pathogen* 4: 431–442.

A safe recombinant Yersinia may be employed in an immunogenic composition to induce an immune response for treating various pathological conditions in mammals. The pathological conditions contemplated by the present invention include tumors and pathogen infections, as disclosed herein.

The immunogenic compositions can include, in addition to a recombinant Yersinia, other substances such as cytokines, adjuvants and pharmaceutically acceptable carriers. Cytokines can also be included in such immunogenic compositions using additional recombinant Yersinia of the present invention capable of delivering a cytokine, for example.

These immunogenic compositions may be administered to the subject in any convenient manner, such as orally, intraperitoneally, intravenously or subcutaneously. Specific immune responses induced by such compositions can lead to the CTL-mediated or antibody-mediated killing of the pathogens or cells with abnormal expression of a relevant antigen, thus alleviating the relevant pathological condition.

The present invention is further illustrated by the following examples.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

EXAMPLE 1

Bacterial Strains, Plasmids and Growth Conditions

The work was carried out with *Y.enterocolitica* E40 (pYV40) (see, M. P. Sory et al. (1995) "Identification of the YopE and YopH domains required for secretion and internalization into the cytosol of macrophages, using the cyaA gene fusion approach" *Proc. Nat'l Acad. Sci. USA* 92: 11998–12002), its isogeneic ampicillin sensitive derivative MRS40(pYV40) (see, M. R. Sarker et al., and their various non-polar mutants. Plasmids are listed in Table 1. Bacteria were grown in Brain Heart Infusion (BHI) (Difco, Detroit, Mich.). After overnight preculture, bacteria were diluted 1/20 in fresh BHI, allowed to grow for 30 minutes at room temperature, and synthesis of the Yop virulon was induced by incubation for 150 minutes at 37° C. before infection.

TABLE 1

Exemplary Antigens

| Gene | MHC | Peptide | Position | SEQ ID NO: |
|---|---|---|---|---|
| MAGE-1 | HLA-A1 | EADPTGHSY | 161–169 | 1 |
|  | HLA-Cw16 | SAYGEPRKL | 230–238 | 2 |
| MAGE-3 | HLA-A1 | EVDPIGHLY | 168–176 | 3 |
|  | HLA-A2 | FLWGPRALV | 271–279 | 4 |
|  | HLA-B44 | MEVDPIGHLY | 167–176 | 5 |
| BAGE | HLA-Cw16 | AARAVFLAL | 2–10 | 6 |
| GAGE-1,2 | HLA-Cw16 | YRPRPRRY | 9–16 | 7 |
| RAGE | HLA-B7 | SPSSNRIRNT | 11–20 | 8 |
| GnT-V | HLA-A2 | VLPDVFIRC(V) | 2–10/11 | 9 |
| MUM-1 | HLA-B44 | EEKLIVVLF | exon 2/intron | 10 |
|  |  | EEKLSVVLF (wild type) |  | 11 |
| CDK4 | HLA-A2 | ACDPHSGHFV | 23–32 | 12 |
|  |  | ARDPHSGHFV (wild type) | 13 |  |
| β-catenin | HLA-A24 | SYLDSGIHF | 29–37 | 14 |
|  |  | SYLDSGIHS (wild type) |  | 15 |
| Tyrosinase | HLA-A2 | MLLAVLYCL | 1–9 | 16 |
|  | HLA-A2 | YMNGTMSQV | 369–377 | 17 |
|  | HLA-A2 | YMDGTMSQV | 369–377 | 18 |
|  | HLA-A24 | AFLPWHRLF | 206–214 | 19 |
|  | HLA-B44 | SEIWRDIDF | 192–200 | 20 |
|  | HLA-B44 | YEIWRDIDF | 192–200 | 21 |
|  | HLA-DR4 | QNILLSNAPLGPQFP | 56–70 | 22 |
|  | HLA-DR4 | DYSYLQDSDPDSFQD | 448–462 | 23 |
| Melan-A$^{MART-1}$ | HLA-A2 | (E)AAGIGILTV | 26/27–35 | 24 |
|  | HLA-A2 | ILTVILGVL | 32–40 | 25 |
| gp100$^{Pme1117}$ | HLA-A2 | KTWGQYWQV | 154–162 | 26 |
|  | HLA-A2 | ITDQVPFSV | 209–217 | 27 |
|  | HLA-A2 | YLEPGPVTA | 280–288 | 28 |
|  | HLA-A2 | LLDGTATLRL | 457–466 | 29 |
|  | HLA-A2 | VLYRYGSFSV | 476–485 | 30 |
| DAGE | HLA-A24 | LYVDSLFFL | 301–309 | 31 |
| MAGE-6 | HLA-Cw16 | KISGGPRISYPL | 292–303 | 32 |

EXAMPLE 2

Construction of the Polymutant Strains

To construct the yopHOPEM polymutant strain, the yopE, yopH, yopO, yopM and yopP genes were successively knocked out by allelic exchange in the MRS40 strain using the suicide vectors pMRS101 and pKNG101. See, K. Kaniga et al. (1991) "A wide-host range suicide vector for improving reverse genetics in gram-negative bacteria: inactivation of the blaA gene of *Yersinia enterocolitica*" Gene 109: 137–141 and M. R. Sarker et al. (1997) "An improved version of suicide vector pKNG101 for gene replacement in Gram-negative bacteria" *Mol. Microbiol.* 23: 409–411. The various deletions are described in Table 2 in the "suicide vectors and mutators" section. The YopE gene was first mutated using the mutator pPW52 (see, P. Wattiau et al. (1993) "SycE, a chaperone-like protein of *Yersinia enterocolitica* involved in the secretion of YopE" *Mol. Microbiol.* 8: 123–131), giving strain MRS40(pAB4052). Mutation of the YopH gene in this strain with the mutator pAB31 (see, S.D. Mills et al. (1997) "*Yersinia enterocolitica* induces apoptosis in macrophages by a process requiring functional type III secretion and translocation mechanisms and involving YopP, presumably acting as an effector protein" *Proc. Natl. Acad. Sci. USA* 94: 12638–12643) gave the double yopEH mutant MRS40(pAB404). The triple yopEHO mutant MRS40(pAB405) was then obtained by allelic exchange with the mutator pAB34 (see, S. D. Mills et al., 1997). The YopP gene was then mutated with mutator pMSK7 (see S. D. Mills et al. (1997)), leading to the yopEHOP mutant MRS40(pMSK46). The yopHOPEM strain MRS40(pABL403) was finally obtained by allelic exchange with the yopM mutator pAB38 (see, S. D. Mills et al., 1997).

TABLE 2

Plasmids

| Plasmids | Relevant Characteristics | References |
|---|---|---|
| pYV pABL403 | pYV40 yopE$_{21}$, yopHΔ$^{1-352}$ yopOΔ$^{65-558}$, yopP$_{23}$, yopM$_{23}$ Suicide Vectors and mutators | see Example 2 of the present specification |
| pKNG101 | $^{ori}$R6K $^{sac}$BR+ $^{on}$TRK2 $^{str}$AB+ | K. Kaniga et al. (1991) Gene 109:137–141. |
| pMRS101 | $^{ori}$R6K $^{sac}$BR+ $^{on}$TRK2 $^{str}$AB+ $^{ori}$ColE1$_{bla}$+ | M. R. Sarker and G. R. Cornelis (1997) Mol. Microbiol. 23:409–411. |
| pAB31 | pMRS101 yopHΔ$_{1-352}$+ | S. D. Mills et al. (1997) Proc. Natl. Acad. Sci. USA 94:12638–12643. |
| pAB34 | pMRS101 yopOΔ$_{65-558}$+ | S. D. Mills et al. (1997) |
| pAB38 | pMRS101 yopM$_{23}$+ | S. D. Mills et al. (1997) |
| pMSK7 | pMRS101 yopP$_{23}$+ | S. D. Mills et al. (1997) |
| pPW52 | pKNG101 yopE$_{21}$+ | P. Waattiau and G. R. Cornelis (1993) Mol. Microbiol. 8:123–131. |

EXAMPLE 3

Construction of a Plasmid Encoding YopE$_{130}$-MAGE-1 and Introduction of this Plasmid into Yersinia The sequence encoding protein MAGE-1 was inserted in frame with a sequence encoding a truncated YopE, YopE$_{130}$ containing the first 130 amino acids of YopE. Such a plasmid is graphically depicted in FIG. 1.

The open reading frame of MAGE-1 was amplified by PCR using a MAGE-1 cDNA cloned in pcDNAI/Amp (Invitrogen, Carlsbad, Calif.) as template. The upstream primer, AAACTGCAGATGTCTCTTGAGCAGAGGAGTC, (SEQ ID NO:38), consisted of the first nucleotides of the open reading frame of MAGE-1 preceded by a PstI site. The downstream primer, AAACTGCAGTCAGACTCCCTCTTCCTCCTC, (SEQ ID NO:39), consisted of nucleotides complementary to the last nucleotides of the open reading frame of MAGE-1 followed by a PstI site. See FIG. 1. The PCR product was digested with PstI and inserted in frame with the truncated YopE at the PstI site of vector pMS111 (see, Sory et al. (1994) *Molecular Microbiology* 14: 583–594). pMS111-MAGE-1 was electroporated in bacteria strain DH5αF'IQ. DNA was extracted from some clones and the DNA of a positive recombinant clone was electroporated in bacteria strain SM10. After mobilization of pMS111 from SM10 in Yersinia MRS40 (pABL403), recombinant clones were then selected on agar-containing medium, supplemented with nalidixic acid, sodium-arsenite and chloramphenicol. MRS40 is an isogeneic derivative of E40 sensitive to ampicillin (see, Sory et al. (1995) *Proc. Natl. Acad. Sci. USA* 92: 11998–12002).

EXAMPLE 4

Targeting EBV-Transformed B Cells

One colony of Yersinia MRS40 (pABL403) containing pMS111-MAGE-1 was then grown overnight at 28° C. in LB medium supplemented with nalidixic acid, sodium m-arsenite and chloramphenicol. The overnight culture was diluted in fresh medium in order to obtain an OD (optical desity) of 0.2. The fresh culture was amplified at 28° C. for approximately 2 hours. The bacteria were washed in 0.9% NaCl and resuspended at $10^8$ bacteria per ml in 0.9% NaCl. 50,000 EBV-transformed HLA-A1$^+$ B cells (KASOII-EBV) were placed in microwells (96 wells round-bottomed) and pelleted by centrifugation. The supernatant was discarded and various dilutions of bacteria were added in 100 ul of complete RPMI 1640 (culture media was supplemented with 10% FCS and with L-arginine (116 mg/ml), L-asparagine (36 mg/ml), L-glutamine (216 mg/ml). Two hours after infection, gentamicin (30 μg/ml) was added for the next two hours, and the cells were finally washed three times.

As a negative control, the same cells were also infected with Yersinia MRS40 (pABL403) containing pMS621, a plasmid which encodes only the truncated YopE, i.e., YopE$_{130}$.

EXAMPLE 5

Recognition of Targeted B Cells by MZ2-CTL 82/30

Figure 2A:
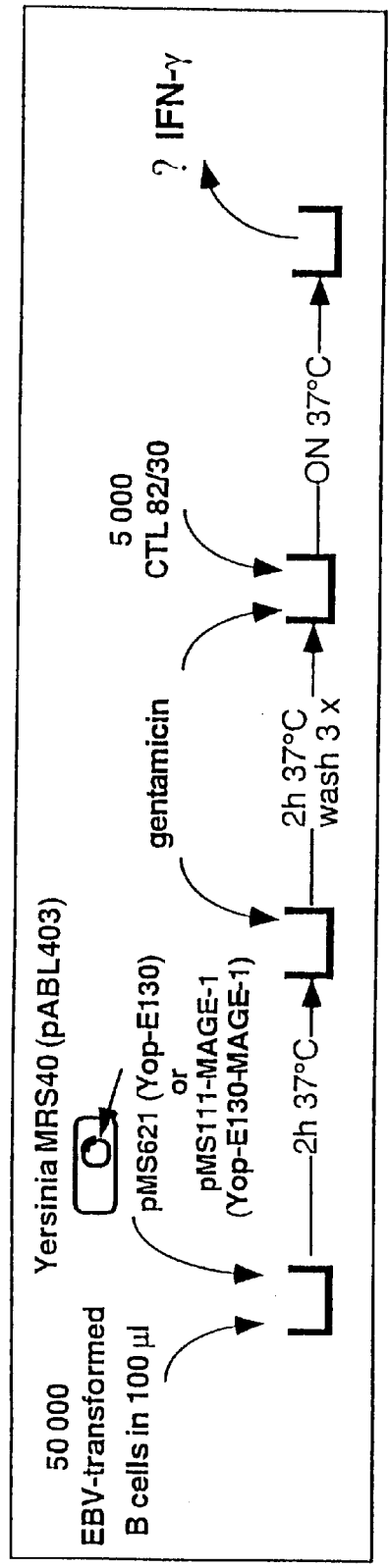

MZ2-CTL 82/30 are specific for the MAGE-1 peptide EADPTGHSY which is presented by HLA-A1 (U.S. Pat. No. 5,342,774). 5000 MZ2-CTL 82/30 cells were added in each microwell containing the Yersinia in a final volume of 100 μl of Iscove's complete medium (culture medium was supplemented with 10% human serum, L-arginine (116 mg/ml), L-asparagine (36 mg/ml), L-glutamine (216 mg/ml), streptomycine (0.1 mg/ml), penicillin (200 U/ml), IL-2 (25 U/ml) and gentamicin (15 μg/ml). After overnight incubation, the presence of IFN-gamma (that is produced by CTL upon activation) in the supernatant of the co-culture was tested in a standard ELISA assay (Biosource, Fleurus, Belgium). FIG. 2A graphically depicts such a procedure.

Figure 2B:
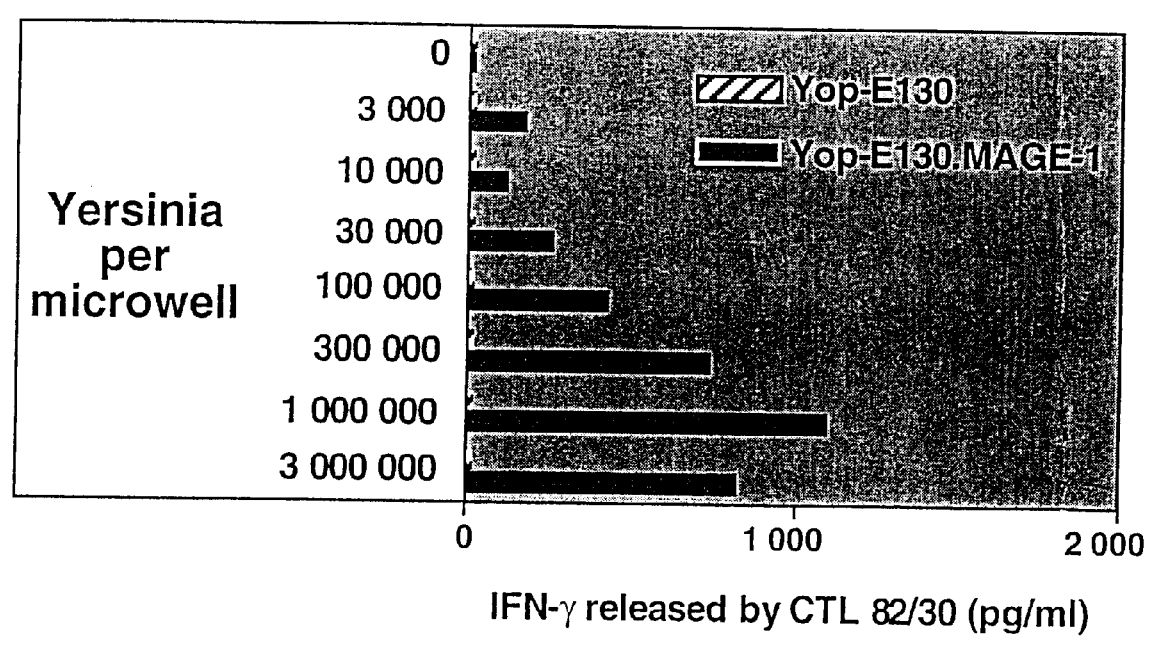

As indicated in FIG. 2B, the HLA-A1$^+$ B cells infected with Yersinia encoding YopE$_{130}$-MAGE-1 were recognized by the CTL 82/30, while the same cells infected with the control plasmid YopE$_{130}$ were not. The optimal concentration of bacteria is around 1,000,000 per microwell.

What is claimed is:

1. An isolated mutant Yersinia strain having the designation of *Y. enterocolitica* yopEHOMP or *Y. pseudotuberculosis* yopEHAMJ.

2. The isolated quintuple mutant Yersinia strain according to claim 1, having the designation of *Yersinia enterocolitica* MRS40 (pABL403).

3. An expression vector for delivering a heterologous protein into a eukaryotic cell, which comprises in the 5' to 3' direction:
   a promoter from a Yersinia virulon gene;
   a first DNA sequence encoding a delivery signal from a Yersinia effector protein, operably linked to said promoter; and
   a second DNA sequence coding for said heterologous protein, fused in frame to the 3' end of said first DNA sequence.

4. The expression vector of claim 3, wherein said Yersinia virulon gene is a Yersinia effector-encoding gene.

5. The expression vector of claim 4, wherein said effector-encoding gene is selected from the group consisting of YopE, YopH, YopO, YopM and YopP of *Y. enterocolitica;* and YopE, YopH, YpkA, YopM and YopJ of *Y. pseudotuberculosis*.

6. The expression vector of claim 5, wherein said effector-encoding gene is *Y. enterocolitica* of YopE.

7. The expression vector of claim 3, wherein said effector protein is selected from the group consisting of YopE, YopH, YopO, YopM and YopP of *Yersinia enterocolitica;* and YopE, YopH, YpkA, YopM and YopJ of *Y. pseudotuberculosis*.

8. The expression vector of claim 7, wherein said effector protein is one of *Yersinia enterocolitica* YopE or *Y. pseudotuberculosis* YopE.

9. The expression vector of claim 3, wherein said delivery signal is *Y. enterocolitica* YopE$_{130}$.

10. The expression vector of claim 3, wherein said heterologous protein comprises at least one epitope of a naturally occurring protein.

11. The expression vector of claim 10, wherein said naturally occurring protein is a tumor associated protein or a pathogen antigen.

12. The expression vector of claim 11, wherein said tumor associated protein is selected from the group consisting of members of the MAGE family, the BAGE family, the DAGE/Prame family, the GAGE family, the RAGE family, the SMAGE family, NAG, Tyrosinase, Melan-A/MART-1, gp100, MUC-1, TAG-72, CA125, p21ras, p53, HPV16 E7, HOM-MEL-40, HOM-MEL-55, NY-COL-2, HOM-HD-397, HOM-RCC-1.14, HOM-HD-21, HOM-NSCLC-11, HOM-MEL-2.4, and HOM-TES-11.

13. The expression vector of claim 12, wherein said tumor-associated protein is MAGE-1.

14. An isolated mutant Yersinia for delivery of a heterologous protein into a eukaryotic cell, wherein said Yersinia comprises at least one mutation in at least one Yersinia effector-encoding gene; and wherein said Yersinia is deficient in the production of at least one functional effector protein and is transformed with an expression vector which comprises, in the 5' to 3' direction:
   a promoter from a Yersinia virulon gene;
   a first DNA sequence encoding a delivery signal from a Yersinia effector protein, operably linked to said promoter; and
   a second DNA sequence coding for said heterologous protein, fused in frame to the 3' end of said first DNA sequence.

15. The Yersinia according to claim 14, wherein said Yersinia virulon gene is a Yersinia effector-encoding gene.

16. The Yersinia according to claim 15, wherein said effector-encoding gene is selected from the group consisting of YopE, YopH, YopO, YopM and YopP of *Y. enterocolitica;* and YopE, YopH, YpkA, YopM and YopJ of *Y. pseudotuberculosis*.

17. The Yersinia according to claim 16, wherein said effector-encoding gene is *Y. enterocolitica* YopE.

18. The Yersinia according to claim 14, wherein said effector protein selected from the group consisting of YopE, YopH, YopO, YopM and YopP of *Yersinia enterocolitica;* and YopE, YopH, YpkA, YopM and YopJ of *Y. pseudotuberculosis.*

19. The Yersinia according to claim 18, wherein said effector protein is one of *Yersinia enterocolitica's* YopE or *Y. pseudotuberculosis's* YopE.

20. The Yersinia according to claim 14, wherein said delivery signal is *Y. enterocolitica* YopE$_{130}$.

21. The Yersinia according to claim 14, wherein said heterologous protein comprises at least one epitope of a naturally occurring protein.

22. The Yersinia according to claim 21, wherein said naturally occurring protein is a tumor-associated protein or a pathogen antigen.

23. The Yersinia according to claim 22, wherein said tumor-associated protein is selected from the group consisting of members of the MAGE family, the BAGE family, the DAGE/Prame family, the GAGE family, the RAGE family, the SMAGE family, NAG, Tyrosinase, Melan-A/MART-1, gp100, MUC-1, TAG-72, CA125, p21ras, p53, HPV16 E7, HOM-MEL-40, HOM-MEL-55, NY-COL-2, HOM-HD-397, HOM-RCC-1.14, HOM-HD-21, HOM-NSCLC-11, HOM-MEL-2.4, and HOM-TES-11.

24. The Yersinia according to claim 23, wherein said tumor-associated protein is MAGE-1.

25. The Yersinia according to claim 14, wherein said effector encoding gene is selected from the group consisting of YopE, YopH, YopO, YopM and YopP of *Y. enterocolitica;* and YopE, YopH, YpkA, YopM and YopJ of *Y. pseudotuberculosis.*

26. The Yersinia according to claim 14, wherein said mutation is a mutation of the promoter sequence of said effector gene.

27. The Yersinia according to claim 14, wherein said mutation is a mutation of the coding sequence of said effector gene.

28. The Yersinia according to claim 14, wherein said Yersinia is *Y. enterocolitica* yopEHOMP transformed with said expression vector or *Y. pseudotuberculosis* yopEHAOJ transformed with said expression vector.

29. The Yersinia according to claim 14, wherein said Yersinia is *Yersinia enterocolitica* MRS40 (pABL403) transformed with said expression vector.

30. A method for delivering a heterologous protein into a eukaryotic cell in vitro, comprising contacting said eukaryotic cell with a Yersinia, wherein said Yersinia comprises at least one mutation in at least one Yersinia effector-encoding gene; and wherein said Yersinia is deficient in the production of at least one functional effector protein and is transformed with an expression vector characterized by, in 5' to 3' direction:
   a promoter from a Yersinia virulon gene;
   a first DNA sequence encoding a delivery signal from a Yersinia effector protein, operably linked to said promoter; and
   a second DNA sequence coding for said heterologous protein, fused in frame to the 3' end of said first DNA sequence.

31. The method of claim 30, wherein said eukaryotic cell is an antigen presenting cell.

32. The method of claim 31, wherein said antigen presenting cell is selected from the group consisting of a B cell, a macrophage, a dendritic cell, a monocyte, a follicular cell, and a fibroblast.

33. The method of claim 31, wherein said antigen presenting cell expresses an MHC molecule capable of presenting one or more epitopes derived from said heterologous protein.

34. The method of claim 30, wherein said effector protein is selected from the group consisting of YopE, YopH, YopO, YopM and YopP of *Yersinia enterocolitica;* and YopE, YopH, YpkA, YopM and YopJ of *Y. pseudotuberculosis.*

35. The method of claim 34, wherein said effector protein is one of *Yersinia enterocolitica* yopE or *Y. pseudotuberculosis* YopE.

36. The method of claim 30, wherein said effector protein is YopE$_{130}$ of *Yersinia enterocolitica.*

37. The method of claim 30, wherein said heterologous protein comprises at least one epitope of a naturally occurring protein.

38. The method of claim 37, wherein said naturally occurring protein is a tumor associated protein or a pathogen antigen.

39. The method of claim 38, wherein said tumor associated protein is selected from the group consisting of members of the MAGE family, the BAGE family, the DAGE/Prame family, the GAGE family, the RAGE family, the SMAGE family, NAG, Tyrosinase, Melan-A/MART-1, gp100, MUC-1, TAG-72, CA125, p21ras, p53, HPV16 E7, HOM-MEL-40, HOM-MEL-55, NY-COL-2, HOM-HD-397, HOM-RCC-1.14, HOM-HD-21, HOM-NSCLC-11, HOM-MEL-2.4, and HOM-TES-11.

40. The method of claim 39, wherein said tumor-associated protein is MAGE-1.

41. The method of claim 30, wherein said Yersinia virulon gene is a Yersinia effector-encoding gene.

42. The method of claim 41, wherein said effector-encoding gene is selected from the group consisting of YopE, YopH, YopO, YopM and YopP of *Y. enterocolitica;* and YopE, YopH, YpkA, YopM and YopJ of *Y. pseudotuberculosis.*

43. The method of claim 42, wherein said effector-encoding gene is YopE of *Y. enterocolitica.*

44. The method of claim 30, wherein said effector encoding gene is selected from the group consisting of YopE, YopH, YopO, YopM and YopP of *Y. enterocolitica;* and YopE, YopH, YpkA, YopM and YopJ of *Y. pseudotuberculosis.*

45. The method of claim 30, wherein said mutation is a mutation of the promoter sequence of said effector gene.

46. The method of claim 30, wherein said mutation is a mutation of the coding sequence of said effector gene.

47. The method of claim wherein 30, said Yersinia is *Y. enterocolitica* yopEHOMP transformed with said expression vector, or *Y. pseudotuberculosis* yopEHAOJ transformed with said expression vector.

48. The method of claim 30, wherein said Yersinia is *Yersinia enterocolitica* MRS40 (pABL403) transformed with said expression vector.

49. A method for inducing in vitro, a cell-mediated immune response specific for a heterologous protein, comprising the steps of:
   (a) selecting an antigen presenting cell expressing an MHC molecule capable of presenting at least one epitope of said heterologous protein;
   (b) forming a cell mixture by contacting said antigen presenting cell with a Yersinia, wherein said Yersinia comprises at least one mutation in at least one Yersinia effector-encoding gene; and wherein said Yersinia is deficient in the production of at least one functional effector protein and is transformed with an expression vector characterized by, in 5' to 3' direction:

a promoter from a Yersinia virulon gene;

a first DNA sequence encoding a delivery signal from a Yersinia effector protein, operably linked to said promoter;

a second DNA sequence coding for said heterologous protein, fused in frame to the 3' end of said first DNA sequence; thereby delivering said heterologous protein into said antigen presenting cell; and (c) contacting a sample containing peripheral blood lymphocytes taken from a subject, with the cell mixture formed in step (b) thereby inducing in vitro, a cell-mediated response specific for said heterologous protein.

50. The method of claim 49, wherein said epitope of is from a tumor associated protein.

51. The method of claim 50, wherein said tumor associated protein is selected from the group consisting of members of the MAGE family, the BAGE family, the DAGE/Prame family, the GAGE family, the RAGE family, the SMAGE family, NAG, Tyrosinase, Melan-A/MART-1, gp100, MUC-1, TAG-72, CA125, p21ras, p53, HPV16 E7, HOM-MEL-40, HOM-MEL-55, NY-COL-2, HOM-HD-397, HOM-RCC-1.14, HOM-HD-21, HOM-NSCLC-11, HOM-MEL-2.4, and HOM-TES-11.

52. The method of claim 51, wherein said tumor associated protein is MAGE-1.

53. The method of claim 52, wherein said epitope is from MAGE-1 and said MHC molecule is HLA-A1.

54. The method of claim 49, wherein said effector encoding gene is selected from the group consisting of YopE, YopH, YopO, YopM and YopP of *Y. enterocolitica;* and YopE, YopH, YpkA, YopM and YopJ of *Y. pseudotuberculosis*.

55. The method of claim 49, wherein said mutation is a mutation of the promoter sequence of said effector gene.

56. The method of claim 49, wherein said mutation is a mutation of the coding sequence of said effector gene.

57. The method of claim 49, wherein said Yersinia is *Y. enterocolitica* yopEHOMP transformed with said expression vector, or *Y. pseudotuberculosis* yopEHAOJ transformed with said expression vector.

58. The method of claim 49, wherein said Yersinia is *Yersinia enterocolitica* MRS40 (pABL403) transformed with said expression vector.

59. A method for monitoring a cellular immune response in a subject before, during and after a vaccination regimen, comprising the steps of:

(a) obtaining from said subject an antigen presenting cell expressing an MHC molecule;

(b) forming a cell mixture by contacting said antigen presenting cell with a Yersinia, wherein said Yersinia comprises at least one mutation in at least one Yersinia effector-encoding gene; and wherein said Yersinia is deficient in the production of at least one functional effector protein and is transformed with an expression vector characterized by, in 5' to 3' direction:

a promoter from a Yersinia virulon gene;

a first DNA sequence encoding a delivery signal from a yersinia effector protein, operably linked to said promoter; and a second DNA sequence fused in frame to the 3' end of said first DNA sequence, wherein said second DNA sequence codes for at least one epitope of said antigen which is presented by said MHC molecule of said antigen presenting cell; thereby delivering said heterologous protein into said antigen presenting cell; and (c) contacting a sample containing peripheral blood lymphocytes taken from said subject, with the cell mixture formed in step (b), and assaying for the presence of a cell-mediated immune response specific for said antigen thereby monitoring a cell-mediated immune response in said subject before, during and after a vaccination regimen.

60. The method of claim 59, wherein said effector encoding gene is selected from the group consisting of YopE, YopH, YopO, YopM and YopP of *Y. enterocolitica;* and YopE, YopH, YpkA, YopM and YopJ of *Y. pseudotuberculosis*.

61. The method of claim 59, wherein said mutation is a mutation of the promoter sequence of said effector gene.

62. The method of claim 59, wherein said mutation is a mutation of the coding sequence of said effector gene.

63. The method of claim 59, wherein said Yersinia is *Y. enterocolitica* yopEHOMP transformed with said expression vector, or *Y. pseudotuberculosis* yopEHAOJ transformed with said expression vector.

64. The method of claim 59, wherein said Yersinia is *Yersinia enterocolitica* MRS40 (pABL403) transformed with said expression vector.

* * * * *

SEQUENCE LISTING

<160> NUMBER OF SEQ ID NOS: 39

<210> SEQ ID NO 1
<211> LENGTH: 9
<212> TYPE: PRT
<213> ORGANISM: Human MAGE-1 peptide

<400> SEQUENCE: 1

Glu Ala Asp Pro Thr Gly His Ser Tyr
                5

<210> SEQ ID NO 2
<211> LENGTH: 9
<212> TYPE: PRT
<213> ORGANISM: Human MAGE-1 peptide

<400> SEQUENCE: 2

Ser Ala Tyr Gly Glu Pro Arg Lys Leu
                5

<210> SEQ ID NO 3
<211> LENGTH: 9
<212> TYPE: PRT
<213> ORGANISM: Human MAGE-3 peptide

<400> SEQUENCE: 3

Glu Val Asp Pro Ile Gly His Leu Tyr
                5

<210> SEQ ID NO 4
<211> LENGTH: 9
<212> TYPE: PRT
<213> ORGANISM: Human MAGE-3 peptide

<400> SEQUENCE: 4

Phe Leu Trp Gly Pro Arg Ala Leu Val
                5

<210> SEQ ID NO 5
<211> LENGTH: 10
<212> TYPE: PRT
<213> ORGANISM: Human MAGE-3 peptide

<400> SEQUENCE: 5

Met Glu Val Asp Pro Ile Gly His Leu Tyr
                5                   10

<210> SEQ ID NO 6
<211> LENGTH: 9
<212> TYPE: PRT
<213> ORGANISM: Human BAGE peptide

<400> SEQUENCE: 6

Ala Ala Arg Ala Val Phe Leu Ala Leu
                5

<210> SEQ ID NO 7
<211> LENGTH: 8
<212> TYPE: PRT
<213> ORGANISM: Human GAGE-1,2 peptide

<400> SEQUENCE: 7

Tyr Arg Pro Arg Pro Arg Arg Tyr
                5

```
<210> SEQ ID NO 8
<211> LENGTH: 10
<212> TYPE: PRT
<213> ORGANISM: Human RAGE peptide

<400> SEQUENCE: 8

Ser Pro Ser Ser Asn Arg Ile Arg Asn Thr
                 5                   10

<210> SEQ ID NO 9
<211> LENGTH: 10
<212> TYPE: PRT
<213> ORGANISM: Human GnT-V peptide

<400> SEQUENCE: 9

Val Leu Pro Asp Val Phe Ile Arg Cys Val
                 5                   10

<210> SEQ ID NO 10
<211> LENGTH: 9
<212> TYPE: PRT
<213> ORGANISM: Human MUM-1 peptide

<400> SEQUENCE: 10

Glu Glu Lys Leu Ile Val Val Leu Phe
                 5

<210> SEQ ID NO 11
<211> LENGTH: 9
<212> TYPE: PRT
<213> ORGANISM: Human MUM-1 peptide

<400> SEQUENCE: 11

Glu Glu Lys Leu Ser Val Val Leu Phe
                 5

<210> SEQ ID NO 12
<211> LENGTH: 10
<212> TYPE: PRT
<213> ORGANISM: Human CDK4 peptide

<400> SEQUENCE: 12

Ala Cys Asp Pro His Ser Gly His Phe Val
                 5                   10

<210> SEQ ID NO 13
<211> LENGTH: 10
<212> TYPE: PRT
<213> ORGANISM: Human CDK4 peptide

<400> SEQUENCE: 13

Ala Arg Asp Pro His Ser Gly His Phe Val
                 5                   10

<210> SEQ ID NO 14
<211> LENGTH: 9
<212> TYPE: PRT
<213> ORGANISM: Human  -catenin peptide

<400> SEQUENCE: 14

Ser Tyr Leu Asp Ser Gly Ile His Phe
                 5

<210> SEQ ID NO 15
```

```
<211> LENGTH: 9
<212> TYPE: PRT
<213> ORGANISM: Human  -catenin peptide

<400> SEQUENCE: 15

Ser Tyr Leu Asp Ser Gly Ile His Ser
                  5

<210> SEQ ID NO 16
<211> LENGTH: 9
<212> TYPE: PRT
<213> ORGANISM: Human Tyrosinase peptide

<400> SEQUENCE: 16

Met Leu Leu Ala Val Leu Tyr Cys Leu
                  5

<210> SEQ ID NO 17
<211> LENGTH: 9
<212> TYPE: PRT
<213> ORGANISM: Human Tyrosinase peptide

<400> SEQUENCE: 17

Tyr Met Asn Gly Thr Met Ser Gln Val
                  5

<210> SEQ ID NO 18
<211> LENGTH: 9
<212> TYPE: PRT
<213> ORGANISM: Human Tyrosinase peptide

<400> SEQUENCE: 18

Tyr Met Asp Gly Thr Met Ser Gln Val
                  5

<210> SEQ ID NO 19
<211> LENGTH: 9
<212> TYPE: PRT
<213> ORGANISM: Human Tyrosinase peptide

<400> SEQUENCE: 19

Ala Phe Leu Pro Trp His Arg Leu Phe
                  5

<210> SEQ ID NO 20
<211> LENGTH: 9
<212> TYPE: PRT
<213> ORGANISM: Human Tyrosinase peptide

<400> SEQUENCE: 20

Ser Glu Ile Trp Arg Asp Ile Asp Phe
                  5

<210> SEQ ID NO 21
<211> LENGTH: 9
<212> TYPE: PRT
<213> ORGANISM: Human Tyrosinase peptide

<400> SEQUENCE: 21

Tyr Glu Ile Trp Arg Asp Ile Asp Phe
                  5

<210> SEQ ID NO 22
<211> LENGTH: 15
<212> TYPE: PRT
<213> ORGANISM: Human Tyrosinase peptide
```

<400> SEQUENCE: 22

Gln Asn Ile Leu Leu Ser Asn Ala Pro Leu Gly Pro Gln Phe Pro
                5                   10                  15

<210> SEQ ID NO 23
<211> LENGTH: 15
<212> TYPE: PRT
<213> ORGANISM: Human Tyrosinase peptide

<400> SEQUENCE: 23

Asp Tyr Ser Tyr Leu Gln Asp Ser Asp Pro Asp Ser Phe Gln Asp
                5                   10                  15

<210> SEQ ID NO 24
<211> LENGTH: 10
<212> TYPE: PRT
<213> ORGANISM: Human Melan-AMART-1 peptide

<400> SEQUENCE: 24

Glu Ala Ala Gly Ile Gly Ile Leu Thr Val
                5                   10

<210> SEQ ID NO 25
<211> LENGTH: 9
<212> TYPE: PRT
<213> ORGANISM: Human Melan-AMART-1 peptide

<400> SEQUENCE: 25

Ile Leu Thr Val Ile Leu Gly Val Leu
                5

<210> SEQ ID NO 26
<211> LENGTH: 9
<212> TYPE: PRT
<213> ORGANISM: Human gp100Pmel117 peptide

<400> SEQUENCE: 26

Lys Thr Trp Gly Gln Tyr Trp Gln Val
                5

<210> SEQ ID NO 27
<211> LENGTH: 9
<212> TYPE: PRT
<213> ORGANISM: Human gp100Pmel117 peptide

<400> SEQUENCE: 27

Ile Thr Asp Gln Val Pro Phe Ser Val
                5

<210> SEQ ID NO 28
<211> LENGTH: 9
<212> TYPE: PRT
<213> ORGANISM: Human gp100Pmel117 peptide

<400> SEQUENCE: 28

Tyr Leu Glu Pro Gly Pro Val Thr Ala
                5

<210> SEQ ID NO 29
<211> LENGTH: 10
<212> TYPE: PRT
<213> ORGANISM: Human gp100Pmel117 peptide

<400> SEQUENCE: 29

-continued

```
Leu Leu Asp Gly Thr Ala Thr Leu Arg Leu
                5                   10

<210> SEQ ID NO 30
<211> LENGTH: 10
<212> TYPE: PRT
<213> ORGANISM: Human gp100Pmel117 peptide

<400> SEQUENCE: 30

Val Leu Tyr Arg Tyr Gly Ser Phe Ser Val
                5                   10

<210> SEQ ID NO 31
<211> LENGTH: 9
<212> TYPE: PRT
<213> ORGANISM: Human DAGE peptide

<400> SEQUENCE: 31

Leu Tyr Val Asp Ser Leu Phe Phe Leu
                5

<210> SEQ ID NO 32
<211> LENGTH: 12
<212> TYPE: PRT
<213> ORGANISM: Human MAGE-6 peptide

<400> SEQUENCE: 32

Lys Ile Ser Gly Gly Pro Arg Ile Ser Tyr Pro Leu
                5                   10

<210> SEQ ID NO 33
<211> LENGTH: 1330
<212> TYPE: DNA
<213> ORGANISM: Yersinia enterocolitica

<400> SEQUENCE: 33
aaaaatggcc aaaaactttc aatggtagaa gagctaaatt tggataagta acgcataaaa     60
attttcgacg aaaaactata tatatatata tatttaatat gtatggtttc atttgcaatg    120
aaaaaaccga taataaagat attttcagaa aggcattcaa tatgtttata aacccaagaa    180
atgtatctaa tacttttttg caagaaccat tacgtcattc ttctgattta actgagatgc    240
cagttgaggc agaaaatgtt aaatctaagg ctgaatatta taatgcatgg tcggaatggg    300
aacgaaatgc ccctccgggg aatggtgaac agaggggaat ggcggtttca aggttacgcg    360
attgcctgga ccgacaagcc catgagctag aactaaataa tctggggctg agttctttgc    420
cggaattacc tccgcattta gagagtttag tggcgtcatg taattctctt acagaattac    480
cggaattgcc gcagagcctg aaatcacttc aagttgataa taacaatctg aaggcattat    540
ccgatttacc tcctttactg gaatatttag gtgccgctaa taatcagctg gaagaattac    600
cagagttgca aaactcgtcc ttcttgacat ctattgatgt tgataacaat tcactgaaaa    660
cattacctga tttacctcct tcactggaat ttcttgctgc tggtaataat cagctggaag    720
aattgtcaga gttgcaaaac ttgcccttct tgactgcgat ttatgctgat aacaattcac    780
tgaaaacatt acccgattta ccccccttccc tgaaaacact taatgtcaga gaaaattatt    840
taactgatct gccagaatta ccgcagagtt taaccttctt agatgtttct gataatattt    900
tttctggatt atcggaattg ccaccaaact tgtataatct caatgcatcc agcaatgaaa    960
taagatcttt atgcgattta ccccccttcac tggtagaact tgatgtcaga gataatcagt   1020
tgatcgaact gccagcgtta cctccacgct tagaacgttt aatcgcttca tttaatcatc   1080
```

```
ttgctgaagt acctgaattg ccgcaaaacc tgaaactgct ccacgtagag tacaacgctc    1140
tgagagagtt tcccgatata cctgagtcag tggaagatct tcggatggac tctgaacgtg    1200
taattgatcc atatgaattt gctcatgaga ctatagacaa acttgaagat gatgtatttg    1260
agtagtgcgc aagagcgttc ataattctgc gtcacgttaa aatatcatta caacgtaatc    1320
actttatcga                                                           1330

<210> SEQ ID NO 34
<211> LENGTH: 1152
<212> TYPE: DNA
<213> ORGANISM: Yersinia enterocolitica

<400> SEQUENCE: 34
gaattcccca actttgacac cgataaccgg ttcaatagta tctggaatag acagcgaaag      60
ttgttgaaat aattgagtga tagcttgttc aaatgaatac atttgatctc ctaatagtta    120
gataaaatat caacttaacc aaagcactct cggcagacca tcaattttag cctataattt    180 ttagtttttta ttttgtctaa tataacaaca aaaacagcag cggttttttta tataaccacc    240 ggctattttc ccactaagat aaccttgttt taatagccaa gggaataaat agtcatgaaa    300
atatcatcat ttatttctac atcactgccc ctgccggcat cagtgtcagg atctagcagc    360
gtaggagaaa tgtctgggcg ctcagtctca cagcaaaaaa gtgatcaata tgcaaacaat    420
ctggccgggc gcactgaaag ccctcagggt tccagcttag ccagccgtat cattgagagg    480
ttatcatcaa tggcccactc tgtgattgga tttatccaac gcatgttctc ggaggggagc    540
cataaaccgg tggtgacacc agcactcacg cctgcacaaa tgccaagccc tacgtctttc    600
agtgatagta tcaagcaact tgctgctgag acgctgccaa atacatgca gcagttgagt    660 agcttggatg cagagacgct gcagaaaaat catgaccagt tcgccacggg cagcggccct    720
cttcgtggca gtatcactca atgccaaggg ctgatgcagt tttgtggtgg ggaattgcaa    780
gctgaggcca gtgccatttt aaacacgcct gtttgtggta ttcccttctc gcagtgggga    840
actgttggtg gggcggccag cgcgtacgtc gccagtggcg ttgatctaac gcaggcagca    900
aatgagatca aagggctggg gcaacagatg cagcaattac tgtcattgat gtgatatgga    960
taaaaacaag ggggtagtgt ttcccccttt ttctatcaat attgcgaata tcttcgtccc    1020
tgatctttca ggggcgaatc gttttttagc atgctcattg ttagaatttc tgacttatct    1080
ctcttctgta ttactactca tactctggaa aatcctgagc atttatatct atggattgat    1140
gcagcactcg ag                                                       1152

<210> SEQ ID NO 35
<211> LENGTH: 2000
<212> TYPE: DNA
<213> ORGANISM: Yersinia enterocolitica

<400> SEQUENCE: 35
agggcattgg aattaaaaat atatttatct aaatgatgat gagtttaaat tacatttgcg      60
tattaaaatg aataacgcat tattaacgta ttaccatctg ttcccgctta attttttaaa    120
aaatttaagg taacaatgag tatatatctt atgggaaaag ccaaaaaact aacgaacact    180
ataataattc gattaacatc aatgaaaata cacggctcac ctattattaa aataatacga    240
ctagcattat aagaaaaaat attttttatg tttatagtat aggcgtgtat ttaattagtt    300
cttaatttaa ttaaggaggg aagcatgaac ttatcattaa gcgatcttca tcgtcaggta    360
tctcgattgg tgcagcaaga gagcggtgat tgtaccggga aattaagagg taacgttgct    420
```

-continued

```
gccaataaag aaactacctt tcaaggtttg accatagcca gtggtgccag agagtcagaa    480
aaagtatttg ctcaaactgt actaagccac gtagcaaata ttgttctaac tcaagaagat    540
accgctaagc tattgcaaag cacggtaaag cataatttga ataattatga attaagaagt    600
gtcggcaatg gtaatagtgt acttgtcagt ttacgtagtg accaaatgac actacaagac    660
gccaaagtgc tgttggaggc tgcattgcga caagagtcgg gagcgagggg gcatgtatca    720
tctcattcac attcagtcct tcacgcaccg ggaaccccgg tgcgtgaagg actgcgttca    780
catctagacc ccagaacacc accgttgcca ccgcgtgaac gaccacacac ttctggccat    840
cacggggctg gcgaagccag agccaccgca ccaagcactg tttctcctta tggcccagaa    900
gcgcgcgcag aactcagcag ccgcctcacc acattgcgca atacgctggc gccagcaacg    960
aatgatccgc gttacttaca agcctgcggc ggtgaaaagc taaaccgatt tagagatatt   1020
caatgctgtc ggcaaaccgc agtacgcgcc gatcttaatg ccaattacat ccaggtcggt   1080
aacactcgta ccatagcgtg ccagtatccg ctacaatctc aacttgaaag ccatttccgt   1140
atgctggcag aaaaccgaac gccagtgttg gctgttttag cgtccagttc tgagatagcc   1200
aatcaaagat tcggtatgcc agattatttc cgccagagtg gtacctatgg cagtatcact   1260
gtagagtcta aaatgactca gcaagttggt ctcggtgacg ggattatggc agatatgtat   1320
actttaacga ttcgtgaagc gggtcaaaaa acaatttctg ttcctgtggt tcatgttggc   1380
aattggcccg atcagaccgc agtcagctct gaagttacca aggcactcgc ttcactggta   1440
gatcaaacag cagaaacaaa acgcaatatg tatgaaagca aaggaagttc agcggtagca   1500
gatgactcca aattacggcc ggtaatacat tgccgtgcgg gtgttggccg tactgcgcaa   1560
ctgattggcg caatgtgcat gaatgatagt cgtaatagtc agttaagcgt agaagatatg   1620
gtcagccaaa tgcgagtaca aagaaatggt attatggtac aaaaagatga gcaacttgat   1680
gttctgatta agttggctga aggacaaggg cgaccattat taaatagcta atgtaaatat   1740
ttattcctat gagtaaataa aattactaag agatatacac cactttgcca atcaaagaaa   1800
ctttaaacct caactaaagt aagcaattag ttgaggttta tctgctatag aataattatt   1860
aacaaaaata taaacaacaa aattaaaagt tatgtgtcta cttttacttt atgtaaccaa   1920
acccattaat ggataccgta cgtttttctt ttatagaatt aaaccagtaa atgagatgat   1980
gaaggacgat gatcatcgtc                                               2000
```

<210> SEQ ID NO 36
<211> LENGTH: 867
<212> TYPE: DNA
<213> ORGANISM: Yersinia enterocolitica

<400> SEQUENCE: 36

```
atgattgggc caatatcaca aataaacagc ttcggtggct tatcagaaaa agagacccgt     60
tctttaatca gtaatgaaga gcttaaaaat atcataatac agttggaaac tgatatagcg    120
gatggatcct ggttccataa aaattattca cgcctggata tagaagtcat gcccgcatta    180
gtaattcagg cgaacaataa atatccggaa atgaatctta attttgttac atctccccag    240
gacctttcga tagaaataaa aaatgtcata gaaaatggag ttggatcttc ccgcttcata    300
attaacatgg gggagggtgg aatacatttc agtgtaattg attacaaaca tataaatggg    360
aaaacatctc tgatattatt tgaaccagta aactttaata gtatggggcc agcgatactg    420
gcaataagta caaaaacggc cattgaacgt tatcaattac ctgattgcca tttttccatg    480
gtggaaatgg atattcagcg aagctcatct gaatgtggta tttttagttt ggcactggca    540
```

-continued

```
aaaaaacttt acaccgagag agatagcctg ttgaaaatac atgaagataa tataaaaggt    600
atattaagtg atagtgaaaa tcctttaccc cacaataagt tggatccgta tctcccggta    660
actttttaca aacatactca aggtaaaaaa cgtcttaatg aatatttaaa tactaacccg    720
cagggagttg gtactgttgt taacaaaaaa aatgaaacca tctttaatag gtttgataac    780
aataaatcca ttatagatgg aaaggaatta tcagtttcgg tacataaaaa gagaatagct    840
gaatataaaa cacttctcaa agtataa                                        867
```

<210> SEQ ID NO 37
<211> LENGTH: 2190
<212> TYPE: DNA
<213> ORGANISM: Yersinia enterocolitica

<400> SEQUENCE: 37

```
atgaaaatca tgggaactat gccaccgtcg atctccctcg ccaaagctca tgagcgcatc      60
agccaacatt ggcaaaatcc tgtcggtgag ctcaatatcg gaggaaaacg gtatagaatt    120
atcgataatc aagtgctgcg cttgaacccc cacagtggtt tttctctctt tcgagaaggg    180
gttggtaaga tcttttcggg gaagatgttt aacttttcaa ttgctcgtaa ccttactgag    240
acactccatg cagcccagaa aacgacttcg caggagctaa ggtctgatat ccccaatgct    300
ctcagtaatc tctttggagc caagccacag accgaactgc cgctgggttg gaaagggaag    360
cctttgtcag gagctccgga tcttgaaggg atgcgagtgg ctgaaaccga taagtttgcc    420
gagggcgaaa gccatattag tataatagaa actaaggata atcagcggtt ggtggctaag    480
attgaacgct ccattgccga ggggcatttg ttcgcagaac tggaggctta taaacacatc    540
tataaaaccg cgggcaaaca tcctaatctt gccaatgtcc atggcatggc tgtggtgcca    600
tacggtaacc gtaaggagga agcattgctg atggatgagg tggatggttg gcgttgttct    660
gacacactaa gaagcctcgc cgatagctgg aagcaaggaa agatcaatag tgaagcctac    720
tggggaacga tcaagtttat tgcccatcgg ctattagatg taaccaatca ccttgccaag    780
gcagggatag tacataacga tatcaaaccc ggtaatgtgg tatttgaccg cgctagcgga    840
gagcccgttg tcattgatct aggattacac tctcgttcag gggaacaacc taaggggttt    900
acagaatcct tcaaagcgcc ggagcttgga gtaggaaacc taggcgcatc agaaaagagc    960
gatgtttttc tcgtagtttc aacccttcta catggtatcg aaggttttga gaaagatccg   1020
gagataaagc ctaatcaagg actgagattc attacctcag aaccagcgca cgtaatggat   1080
gagaatggtt acccaatcca tcgacctggt atagctggag tcgagacagc ctatacacgc   1140
ttcatcacag acatccttgg cgtttccgct gactcaagac ctgattccaa cgaagccaga   1200
ctccacgagt tcttgagcga cggaactatt gacgaggagt cggccaagca gatcctaaaa   1260
gatactctaa ccggagaaat gagcccatta tctactgatg taaggcggat aacacccaag   1320
aagcttcggg agctctctga tttgcttagg acgcatttga gtagtgcagc aactaagcaa   1380
ttggatatgg gggtggtttt gtcggatctt gataccatgt tggtgacact cgacaaggcc   1440
gaacgcgagg ggggagtaga caaggatcag ttgaagagtt ttaacagttt gattctgaag   1500
acttacagcg tgattgaaga ctatgtcaaa ggcagagaag gggataccaa gagttccagt   1560
gcggaagtat ccccctatca tcgcagtaac tttatgctat cgatcgccga accttcactg   1620
cagaggatcc aaaagcatct ggaccagaca cactcttttt ctgatatcgg ttcactagtg   1680
cgcgcacata agcacctgga aacgctttta gaggtcttag tcaccttgtc accgcaaggg   1740
cagcccgtgt cctctgaaac ctacagcttc ctgaatcgat tagctgaggc taaggtcacc   1800
```

-continued

```
ttgtcgcagc aattggatac tctccagcag cagcaggaga gtgcgaaacg gcaactatct      1860
attctgatta atcgttcagg ttcttgggcc gatgttgctc gtcagtccct gcagcgtttt      1920
gacagtaccc ggcctgtagt gaaattcggc actgagcagt ataccgcaat tcaccgtcag      1980
atgatggcgg cccatgcagc cattacgcta caggaggtat cggagtttac tgatgatatg      2040
cgaaacttta cagcggactc tattccacta ctgattcgac ttggacgaag cagtttaata      2100
gatgagcatt tggttgaaca gagagagaag ttgcgagacg tgacgaccat cgccgagcga      2160
ctgaaccggt tggagcggga atggatgtga                                       2190

<210> SEQ ID NO 38
<211> LENGTH: 31
<212> TYPE: DNA
<213> ORGANISM: Yersinia enterocolitica

<400> SEQUENCE: 38
aaactgcaga tgtctcttga gcagaggagt c                                        31

<210> SEQ ID NO 39
<211> LENGTH: 30
<212> TYPE: DNA
<213> ORGANISM: Yersinia enterocolitica

<400> SEQUENCE: 39
aaactgcagt cagactccct cttcctcctc                                          30
```